US008440625B2

(12) United States Patent
Tai

(10) Patent No.: US 8,440,625 B2
(45) Date of Patent: May 14, 2013

(54) SECRETED PROTEIN ACIDIC AND RICH IN CYSTEINE (SPARC) AS CHEMOTHERAPEUTIC SENSITIZERS

(75) Inventor: Isabella T. Tai, Vancouver (CA)

(73) Assignee: University of British Columbia, Vancouver, BC (CA)

( * ) Notice: Subject to any disclaimer, the term of this patent is extended or adjusted under 35 U.S.C. 154(b) by 756 days.

(21) Appl. No.: 12/306,804

(22) PCT Filed: Jun. 26, 2007

(86) PCT No.: PCT/CA2007/001150
§ 371 (c)(1), (2), (4) Date: Jun. 4, 2009

(87) PCT Pub. No.: WO2008/000079
PCT Pub. Date: Jan. 3, 2008

(65) Prior Publication Data
US 2009/0305981 A1 Dec. 10, 2009

Related U.S. Application Data

(60) Provisional application No. 60/816,316, filed on Jun. 26, 2006.

(51) Int. Cl.
*A61P 35/00* (2006.01)
(52) U.S. Cl.
USPC .......................................... 514/19.3; 514/1.1
(58) Field of Classification Search .................. None
See application file for complete search history.

(56) References Cited

U.S. PATENT DOCUMENTS

| 4,816,567 | A | 3/1989 | Cabilly et al. |
| 5,003,621 | A | 3/1991 | Gailus |
| 5,776,925 | A | 7/1998 | Young et al. |
| 5,821,337 | A | 10/1998 | Carter et al. |
| 6,001,563 | A | 12/1999 | Deeley et al. |
| 6,387,664 | B1 | 5/2002 | Ikemoto |
| 2003/0099974 | A1 | 5/2003 | Lillie et al. |
| 2003/0157073 | A1 | 8/2003 | Peritt et al. |

FOREIGN PATENT DOCUMENTS

| EP | 1 033 401 A2 | 9/2000 |
| WO | WO 02/00164 A2 | 1/2002 |
| WO | WO 2004/064785 A2 | 8/2004 |
| WO | 2005/079173 A2 | 9/2005 |
| WO | WO 2006/112930 A2 | 10/2006 |
| WO | WO 2008/000079 A1 | 1/2008 |

OTHER PUBLICATIONS

Altschul et al., *J. Mol. Biol.*, "Basic local alignment search tool," 215: 403-410 (1990).
Altschul et al., *Nucleic Acids Res.*, "Gapped BLAST and PSI-BLAST: a new generation of protein database search programs," 25(17): 3389-3402 (1997).
Arber et al., *Gastroenterology*, "Activation of c-K-*ras* mutations in human gastrointestinal tumors," 118: 1045-1050 (2000).
Ausubel et al., *Current Protocols in Molecular Biology*, vol. 1, Wiley & Sons Inc., pp. 2.10.3 (1989).
Bairoch et al., *Nucleic Acids Res.*, "The SWISS-PROT protein sequence database and its supplement TrEMBL in 2000," 28(1): 45-48 (2000).
Bornstein, *J. Cell Biol.*, "Diversity of function is inherent in matricellular proteins: An appraisal of thrombospondin 1," 130 (3): 503-506 (1995).
Brekken et al., *J. Clin. Invest.*,"Enhanced growth of tumors in SPARC null mice is associated with changes in the ECM," 111(4): 487-495 (2003).
Chlenski et al., *Cancer Res.*, "Neuroblastoma angiogenesis is inhibited with a folded synthetic molecule corresponding to the epidermal growth factor-like module of the follistatin domain of SPARC," 64: 7420-7425 (2004).
Clynes et al., *Immunology*, Fc receptors are required in passive and active immunity to melanoma, 95: 652-656 (1998).
De Las Alas et al., *J. Natl. Canc. Inst.*, "Loss of DNA mismatch repair: Effects on the rate of mutation to drug resistance," 89(20): 1537-1541 (1997).
Eddy, *Curr.Opin. Struct. Biol.*, "Hidden Markov models," 6: 361-365 (1996).
U.S. Appl. No. 60/690,159.
Ford et al., *Cytotechnology*, "Pharmacologic circumvention of multidrug resistance," 12: 171-212 (1993).
Hasselaar et al., *J. Cell. Biochem.*, "SPARC antagonizes the effect of basic fibroblast growth factor on the migration of bovine aortic endothelial cells," 49: 272-283 (1992).
Hayashi et al., *Prostate*, "Adenoviral infection of surviving antisense sensitizes prostate cancer cells to etoposide in vivo," 65: 10-19 (2005).
Johnstone et al., *Cell*, "Apoptosis: A link between cancer genetics and chemotherapy," 108: 153-164 (2002).
Junker et al., *Bioinformatics*, "Representation of functional information in the SWISS-PROT Data Bank," 15(12): 1066-1067 (1999).
Kaur et al., *Arch. Pathol. Lab. Med.*, "Survivin and Bcl-2 expression in prostatic adenocarcinomas," 128: 39-43 (2004).
Kozak, *J. Mol. Biol.*, "At last six nucleotides preceding the AUG initiator codon enhance translation in mammalian cells," 196: 947-950 (1987).
Krajewska et al., *Clin. Cancer Res.*, "Elevated expression of inhibitor of apoptosis proteins in prostate cancer," 9: 4914-4925 (2003).
Kupprion et al., *J. Biol. Chem.*, "SPARC (BM-40, Osteonectin) inhibits the mitogenic effect of vascular endothelial growth factor on microvascular endothelial cells," 273(45): 29635-29640 (1998).
Kyte et al., *J. Mol. Biol.*, "A simple method for displaying the hydropathic character of a protein," 157: 105-132 (1982).

(Continued)

*Primary Examiner* — Mark Halvorson
(74) *Attorney, Agent, or Firm* — Leydig, Voit & Mayer, Ltd.

(57) ABSTRACT

The present invention relates to compositions and methods of use thereof for cancer therapy sensitization. Such compositions comprise functional fragments of the nucleotide and/or polypeptide sequences of a Secreted Protein Acidic and Rich in Cysteine (SPARC). The compositions can be used in combination with existing chemotherapeutic agents for treatment of cancers.

11 Claims, 10 Drawing Sheets

OTHER PUBLICATIONS

Lane et al., *J. Cell. Biol.*, "Functional mapping of SPARC: Peptides from two distinct $Ca^{++}$-binding sites modulate cell shape," 111(6): 3065-3076 (1990).
Lane et al., *J. Cell Biol.*, "SPARC is a source of copper-binding peptides that stimulate angiogenesis," 125(4): 929-943 (1994).
Latvala et al., *Exp. Eye Res.*, "Distribution of SPARC protein (Osteonectin) in normal and wounded feline cornea," 63: 579-584 (1996).
Lin et al., *Mol. Pharmacol.*, "Effect of loss of DNA mismatch repair on development of Topotecan-, Gemcitabine-, and Paclitaxel-resistant variants after exposure to Cisplatin," 56: 390-395 (1999).
Mason et al., *EMBO J.*, "Developmental and transformation-sensitive expression of the SPARC gene on mouse chromosome 11," 5(8): 1831-1837 (1986).
Needleman et al., *J. Mol. Biol.*, "A general method applicable to the search for similarities in the amino acid sequence of two proteins," 48: 443-453 (1970).
Patil et al., *AAPS J.*, "DNA-based therapeutics and DNA delivery systems: A comprehensive review," 7(1): E61-E77 (2005).
Porter et al., *J. Histochem. Cytochem.*, "Distribution of SPARC in normal and neoplastic human tissue," 43(8): 791-800 (1995).
Puolakkainen et al., *Mol. Cancer Res.*, "Enhanced growth of pancreatic tumors in SPARC-null mice is associated with decreased deposition of extracellular matrix and reduced tumor cell apoptosis," 2: 215-224 (2004).
Rattan et al., *Protein synthesis, posttranslational modifications, and aging*, vol. 663, Boland eds., Ann. NY Acad. Sci., pp. 48-62 (1992).
Rempel et al., *J. Neurooncol.*, "SPARC modulates cell growth, attachment and migration of U87 glioma cells on brain extracellular matrix proteins," 53: 149-160 (2001).
Sage et al., *J. Biol. Chem.*, "Extracellular proteins that modulate cell-matrix interactions," 266(23): 14831-14834 (1991).
Sage et al., *J. Biol. Chem.*, "Cleavage of the matricellular protein SPARC by matrix metalloproteinase 3 produces polypeptides that influence angiogenesis," 278(39): 37849-37857 (2003).
Schultz et al., *Cancer Res.*, "Secreted protein acidic and rich in cysteine promotes glioma invasion and delays tumor growth in vivo," 62: 6270-6277 (2002).
Seifter et al., *Meth. Enzymol.*, "Analysis for protein modifications and nonprotein cofactors," 182: 626-646 (1990).
Skoudy et al., *Biochem J.*, "Intestinal HT-29 cells with dysfunction of E-cadherin show increased pp60src activity and tyrosine phosphorylation of p120-catenin," 317: 279-284 (1996).
Smith et al., *J. Mol. Biol.*, "Identification of common molecular subsequences," 147: 195-197 (1981).
St. Croix et al., *Nat. Med.*, "Impact of the cyclin-dependent kinase inhibitor $p27^{Kip1}$ on resistance of tumor cells to anticancer agents," 2(11): 1204-1210 (1996).
Strandjord et al., *Am. J. Respir. Cell Mol. Biol.*, "SPARC participates in the branching morphogenesis of developing fetal rat lung," 13: 279-287 (1995).
Taghizadeh et al., *Mol. CancerTher.*, "Synergism between vitamin D and secreted protein acidic and rich in cysteine-induced apoptosis and growth inhibition results in increased susceptibility of therapy-resistant colorectal cancer cells to chemotherapy," 6(1): 309-317 (2007).
Tai et al., *J. Neurochem.*, "Role of Egr-1 in cAMP-dependent protein kinase regulation of the phenylethanolamine N-methyltransferase gene," 76: 1851-1859 (2001).
Tai et al., *Mol. Pharmacol.*, "Glucocorticoid responsiveness of the rat phenylethanolamine N-Methyltransferase gene," 61(6): 1385-1392 (2002).
Tai et al., *J. Clin. Invest.*, "Genome-wide expression analysis of therapy-resistant tumors reveals SPARC as a novel target for cancer therapy," 115(6): 1492-1502 (2005).
Villalobos et al., *BMC Bioinformatics*, "Gene designer: a synthetic biology tool for constructing artificial DNA segments," 7: 285 (2006).
Waldman et al., *Nature*, "Uncoupling of S phase and mitosis induced by anticancer agents in cells lacking p21," 381: 713-716 (1996).
Wold, *Posttranslational Covalent Modifications of Proteins*, Johnson ed., Academic Press, pp. 1-12 (1983).
Yiu et al., *Am. J. Pathol.*, "SPARC (secreted protein acidic and rich in cysteine) induces apoptosis in ovarian cancer cells," 159(2): 609-622 (2001).
Database EMBL Seq. ID No. 4218, EBI Database Accession No. AX888355 (Dec. 17, 2003).
Database EMBL Seq. ID No. 4219, EBI Database Accession No. AX888356 (Dec. 17, 2003).
Database EMBL, EBI Accession No. Q4R5R0 (Jul. 19, 2005).
Aycock et al. Journal of Investigative Dermatology 2004, vol. 123, p. 592-599.
Bradshaw, A.D. et al. PNAS. vol. 100, No. 10, p. 6045-6050, 2003.
Braun et al., Cancer 2004. vol. 100, No. 8, p. 1558-1577.
Chin et al. International Journal of Cancer, 2005. vol. 113, No. 5, p. 789-797.
Chlenski, A. et al. 2006 Int. J. Cancer. 118:310-316.
Dalla-Torre et al. BMC Cancer 2006. v6:237.
Davies et al. Blood, 2003, vol. 102, No. 13, 4504-4511.
Davies et al. Nature, 2002, vol. 417, p. 949-954.
Dermer, Bio/Technology vol. 12 Mar. 1994, p. 320.
Dominguez et al. Journal of Bone and Mineral Research, col. 6, No. 10, 1991, p. 1127-1136.
Fan et al. Diabetes 1990, vol. 39, No. 4, p. 519-522.
Goldenberg et al. Molecular Carcinogenesis 2002, p. 113-124.
Hafner et al. Matrix Biology 1994, vol. 14, p. 733-741.
Jendraschake et al. Genomics 1998, vol. 50, p. 53-60.
Jones et al. Cancer Research 2004, vol. 64, p. 3037-3045.
Krestow et al. Biomat Art Cells & Immob. Biotech, 1992, vol. 20, No. 1, 43-51.
Krestow et al. Transplantation, 1991, No. 51, No. 3 p. 651-655.
Lagan et al. Rheumatology 2005, vol. 44, p. 197-201.
Lum et al., Diabetes 1991, vol. 40, p. 1511-1516.
Lum et al. Transplantation, 1992, vol. 53, No. 6 1180-1183.
Massi, D et al. Human Pathology 1999, vol. 30, No. 3, p. 339-344.
Mok SC. et al. Oncogene, 1996, 12:1895-1901.
Ozdag et al. British Journal of Cancer, 2002, 87, 1162-1165.
Sova et al. Cancer Epidermal Biomarkers Prev 2006, vol. 15, No. 1, p. 114-122.
Sato et al. Oncogene, 2003, vol. 22, p. 5021-5030.
Shi et al. Journal of Biological Chemistry 2004, vol. 279, No. 50, p. 52200-52209.
Srivastava, Clinical Cancer Research 2001, p. 1118.
Tai et al. Carcinogenesis 2005, vol. 26, No. 5, p. 908-915.
Tai et al. FASEB Journal 1993, vol. 7 No. 11, p. 1061-1069.
Villarreal XC et al. Biochemistry 1989, vol. 28, p. 6483-6491.
Wang et al. British Journal of Cancer 2004, vol. 91, p. 1924-1930.
Zhou X. et al, Arthritis & Rheumatism 2002, vol. 46, No. 11, p. 2990-2999.
Database Geneseq Jun. 25, 1998 Jendrashak et al. "Homo sapiens osteonectin (SPARC) gene, promoter region".
GenBank Accession No. J02863 Published 2005.
GenBank Accession No. J03040 Published 1995.
GenBank Accession No. NM_003118.2 Published 1992.
GenBank Accession No. X82259 Published 1995.

SEQUENCE LISTING

```
<160> NUMBER OF SEQ ID NOS: 18

<210> SEQ ID NO 1
<211> LENGTH: 3178
<212> TYPE: DNA
<213> ORGANISM: Homo sapiens

<400> SEQUENCE: 1
gttgcctgtc tctaaacccc tccacattcc cgcggtcctt cagactgccc ggagagcgcg      60
ctctgcctgc cgcctgcctg cctgccactg agggttccca gcaccatgag ggcctggatc     120
ttctttctcc tttgcctggc cgggagggcc ttggcagccc ctcagcaaga agccctgcct     180
gatgagacag aggtggtgga agaaactgtg gcagaggtga ctgaggtatc tgtgggagct     240
aatcctgtcc aggtggaagt aggagaattt gatgatggtg cagaggaaac cgaagaggag     300
gtggtggcgg aaaatccctg ccagaaccac cactgcaaac acggcaaggt gtgcgagctg     360
gatgagaaca cacccccat gtgcgtgtgc caggacccca ccagctgccc agcccccatt      420
ggcgagtttg agaaggtgtg cagcaatgac aacaagacct tcgactcttc ctgccacttc     480
tttgccacaa agtgcaccct ggagggcacc aagaagggcc acaagctcca cctggactac     540
atcgggcctt gcaaatacat ccccccttgc ctggactctg agctgaccga attccccctg     600
cgcatgcggg actggctcaa gaacgtcctg gtcaccctgt atgagaggga tgaggacaac     660
aaccttctga ctgagaagca gaagctgcgg gtgaagaaga tccatgagaa tgagaagcgc     720
ctggaggcag gagaccaccc cgtggagctg ctggcccggg acttcgagaa gaactataac     780
atgtacatct tccctgtaca ctggcagttc ggccagctgg accagcaccc cattgacggg     840
tacctctccc acaccgagct ggctccactg cgtgctcccc tcatccccat ggagcattgc     900
accacccgct ttttcgagac ctgtgacctg gacaatgaca agtacatcgc cctggatgag     960
tgggccggct gcttcggcat caagcagaag gatatcgaca aggatcttgt gatctaaatc    1020
cactccttcc acagtaccgg attctctctt taaccctccc cttcgtgttt cccccaatgt    1080
ttaaaatgtt tggatggttt gttgttctgc ctggagacaa ggtgctaaca tagatttaag    1140
tgaatacatt aacggtgcta aaaatgaaaa ttctaaccca agacatgaca ttcttagctg    1200
```

```
taacttaact attaaggcct tttccacacg cattaatagt cccattttc tcttgccatt      1260 tgtagctttg cccattgtct tattggcaca tgggtggaca cggatctgct gggctctgcc      1320
ttaaacacac attgcagctt caacttttct ctttagtgtt ctgtttgaaa ctaatactta      1380
ccgagtcaga ctttgtgttc atttcattc agggtcttgg ctgcctgtgg gcttccccag       1440
gtggcctgga ggtgggcaaa gggaagtaac agacacacga tgttgtcaag gatggttttg      1500
ggactagagg ctcagtggtg ggagagatcc ctgcagaacc caccaaccag aacgtggttt      1560
gcctgaggct gtaactgaga gaaagattct ggggctgtgt tatgaaaata tagacattct      1620
cacataagcc cagttcatca ccatttcctc ctttaccttt cagtgcagtt tcttttcaca      1680
ttaggctgtt ggttcaaact tttgggagca cggactgtca gttctctggg aagtggtcag      1740
cgcatcctgc agggcttctc ctcctctgtc ttttggagaa ccaggctct tctcaggggc       1800 tctagggact gccaggctgt tcagccagg aaggccaaaa tcaagagtga gatgtagaaa       1860
gttgtaaaat agaaaagtg gagttggtga atcggttgtt cttttcctcac atttggatga      1920 ttgtcataag gtttttagca tgttcctcct tttcttcacc ctcccctttt ttcttctatt      1980
aatcaagaga aacttcaaag ttaatgggat ggtcggatct cacaggctga gaactcgttc      2040
acctccaagc atttcatgaa aaagctgctt cttattaatc atacaaactc tcaccatgat      2100
gtgaagagtt tcacaaatcc ttcaaaataa aagtaatga cttagaaact gccttcctgg       2160
gtgatttgca tgtgtcttag tcttagtcac cttattatcc tgacacaaaa acacatgagc      2220
atacatgtct acacatgact acacaaatgc aaacctttgc aaacacatta tgcttttgca     2280
cacacacacc tgtacacaca caccggcatg tttatacaca gggagtgtat ggttcctgta      2340
agcactaagt tagctgtttt catttaatga cctgtggttt aaccctttg atcactacca       2400 ccattatcag caccagactg agcagctata tcctttatt aatcatggtc attcattcat       2460
tcattcattc acaaaatatt tatgatgtat ttactctgca ccaggtccca tgccaagcac      2520
tggggacaca gttatggcaa agtagacaaa gcatttgttc atttggagct tagagtccag      2580
gaggaataca ttagataatg acacaatcaa atataaattg caagatgtca caggtgtgat      2640
gaagggagag taggagagac catgagtatg tgtaacagga ggacacagca ttattctagt      2700
gctgtactgt tccgtacggc agccactacc cacatgtaac tttttaagat ttaaatttaa      2760
attagttaac attcaaaacg cagctcccca atcacactag caacatttca agtgcttgag      2820
agccatgcat gattagtggt taccctattg aataggtcag aagtagaatc ttttcatcat      2880
cacagaaagt tctattggac agtgctcttc tagatcatca taagactaca gagcactttt      2940
caaagctcat gcatgttcat catgttagtg tcgtattttg agctggggtt ttgagactcc      3000
ccttagagat agagaaacag acccaagaaa tgtgctcaat gcaatgggc cacatacc ta      3060 gatctccaga tgtcatttcc cctctcttat tttaagttat gttaagatta ctaaaacaat      3120
aaaagctcct aaaaaatcaa aaaaaaaaaa aaaaaaaaa aaaaaaaaaa aaaaaaa         3178
```

<210> SEQ ID NO 2
<211> LENGTH: 153
<212> TYPE: DNA
<213> ORGANISM: Homo sapiens

<400> SEQUENCE: 2

```
gcccctcagc aagaagccct gcctgatgag acagaggtgg tggaagaaac tgtggcagag       60
gtgactgagg tatctgtggg agctaatcct gtccaggtgg aagtaggaga atttgatgat      120
ggtgcagagg aaaccgaaga ggaggtggtg gcg                                   153
```

<210> SEQ ID NO 3
<211> LENGTH: 51
<212> TYPE: PRT
<213> ORGANISM: Homo sapiens

<400> SEQUENCE: 3

Ala Pro Gln Gln Glu Ala Leu Pro Asp Glu Thr Glu Val Val Glu Glu
1               5                   10                  15

Thr Val Ala Glu Val Thr Glu Val Ser Val Gly Ala Asn Pro Val Gln
            20                  25                  30

Val Glu Val Gly Glu Phe Asp Asp Gly Ala Glu Glu Thr Glu Glu Glu
        35                  40                  45

Val Val Ala
    50

<210> SEQ ID NO 4
<211> LENGTH: 256
<212> TYPE: DNA
<213> ORGANISM: Homo sapiens

<400> SEQUENCE: 4
gaaaatccct gccagaacca ccactgcaaa cacggcaagg tgtgcgagct ggatgagaac    60
aacaccccca tgtgcgtgtg ccaggacccc accagctgcc cagcccccat tggcgagttt   120
gagaaggtgt gcagcaatga caacaagacc ttcgactctt cctgccactt ctttgccaca   180
aagtgcaccc tggagggcac caagaagggc cacaagctcc acctggacta catcgggcct   240
tgcaaataca tcccccc                                                  256

<210> SEQ ID NO 5
<211> LENGTH: 85
<212> TYPE: PRT
<213> ORGANISM: Homo sapiens

<400> SEQUENCE: 5

Glu Asn Pro Cys Gln Asn His Cys Lys His Gly Lys Val Cys Glu
1               5                   10                  15

Leu Asp Glu Asn Asn Thr Pro Met Cys Val Cys Gln Asp Pro Thr Ser
            20                  25                  30

Cys Pro Ala Pro Ile Gly Glu Phe Glu Lys Val Cys Ser Asn Asp Asn
        35                  40                  45

Lys Thr Phe Asp Ser Ser Cys His Phe Phe Ala Thr Lys Cys Thr Leu
    50                  55                  60

Glu Gly Thr Lys Lys Gly His Lys Leu His Leu Asp Tyr Ile Gly Pro
65                  70                  75                  80

Cys Lys Tyr Ile Pro
            85

<210> SEQ ID NO 6
<211> LENGTH: 450
<212> TYPE: DNA
<213> ORGANISM: Homo sapiens

<400> SEQUENCE: 6
cttgcctgga ctctgagctg accgaattcc ccctgcgcat gcgggactgg ctcaagaacg    60
tcctggtcac cctgtatgag agggatgagg acaacaacct tctgactgag aagcagaagc   120
tgcgggtgaa gaagatccat gagaatgaga agcgcctgga ggcaggagac caccccgtgg   180
agctgctggc ccgggacttc gagaagaact ataacatgta catcttccct gtacactggc   240

```
agttcggcca gctggaccag caccccattg acgggtacct ctcccacacc gagctggctc    300
cactgcgtgc tcccctcatc cccatggagc attgcaccac ccgcttttc gagacctgtg     360 acctggacaa tgacaagtac atcgccctgg atgagtgggc cggctgcttc ggcatcaagc    420
agaaggatat cgacaaggat cttgtgatct                                     450
```

<210> SEQ ID NO 7
<211> LENGTH: 149
<212> TYPE: PRT
<213> ORGANISM: Homo sapiens

<400> SEQUENCE: 7

```
Cys Leu Asp Ser Glu Leu Thr Glu Phe Pro Leu Arg Met Arg Asp Trp
1               5                   10                  15

Leu Lys Asn Val Leu Val Thr Leu Tyr Glu Arg Asp Glu Asp Asn Asn
            20                  25                  30

Leu Leu Thr Glu Lys Gln Lys Leu Arg Val Lys Lys Ile His Glu Asn
        35                  40                  45

Glu Lys Arg Leu Glu Ala Gly Asp His Pro Val Glu Leu Leu Ala Arg
    50                  55                  60

Asp Phe Glu Lys Asn Tyr Asn Met Tyr Ile Phe Pro Val His Trp Gln
65                  70                  75                  80

Phe Gly Gln Leu Asp Gln His Pro Ile Asp Gly Tyr Leu Ser His Thr
                85                  90                  95

Glu Leu Ala Pro Leu Arg Ala Pro Leu Ile Pro Met Glu His Cys Thr
            100                 105                 110

Thr Arg Phe Phe Glu Thr Cys Asp Leu Asp Asn Asp Lys Tyr Ile Ala
        115                 120                 125

Leu Asp Glu Trp Ala Gly Cys Phe Gly Ile Lys Gln Lys Asp Ile Asp
    130                 135                 140

Lys Asp Leu Val Ile
145
```

<210> SEQ ID NO 8
<211> LENGTH: 23
<212> TYPE: PRT
<213> ORGANISM: Homo sapiens

<400> SEQUENCE: 8

```
Ala Pro Gln Gln Glu Ala Leu Pro Asp Glu Thr Glu Val Val Glu Glu
1               5                   10                  15

Thr Val Ala Glu Val Thr Glu
            20
```

<210> SEQ ID NO 9
<211> LENGTH: 31
<212> TYPE: PRT
<213> ORGANISM: Homo sapiens

<400> SEQUENCE: 9

```
Cys Gln Asn His His Cys Lys His Gly Lys Val Cys Glu Leu Asp Glu
1               5                   10                  15

Asn Asn Thr Pro Met Cys Val Cys Gln Asp Pro Thr Ser Cys Pro
            20                  25                  30
```

<210> SEQ ID NO 10
<211> LENGTH: 303
<212> TYPE: PRT
<213> ORGANISM: Homo sapiens

```
<400> SEQUENCE: 10

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Thr Glu Thr Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Asn Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 11
<211> LENGTH: 69
<212> TYPE: DNA
<213> ORGANISM: Homo sapiens

<400> SEQUENCE: 11
gcccctcagc aagaagccct gcctgatgag acagaggtgg tggaagaaac tgtggcagag    60
gtgactgag                                                            69

<210> SEQ ID NO 12
<211> LENGTH: 93
<212> TYPE: DNA
<213> ORGANISM: Homo sapiens

<400> SEQUENCE: 12
tgccagaacc accactgcaa acacggcaag gtgtgcgagc tggatgagaa caacacccccc    60
```
atgtgcgtgt gccaggaccc caccagctgc cca         93

```
<210> SEQ ID NO 13
<211> LENGTH: 35
<212> TYPE: PRT
<213> ORGANISM: Homo sapiens

<400> SEQUENCE: 13
```

Glu Ser Ala Leu Cys Leu Pro Pro Ala Cys Leu Pro Leu Arg Val Pro
1               5                   10                  15

Ser Thr Met Arg Ala Trp Ile Phe Phe Leu Leu Cys Leu Ala Gly Arg
            20                  25                  30

Ala Leu Ala
        35

```
<210> SEQ ID NO 14
<211> LENGTH: 17
<212> TYPE: PRT
<213> ORGANISM: Homo sapiens

<400> SEQUENCE: 14
```

Met Arg Ala Trp Ile Phe Phe Leu Leu Cys Leu Ala Gly Arg Ala Leu
1               5                   10                  15

Ala

```
<210> SEQ ID NO 15
<211> LENGTH: 27
<212> TYPE: PRT
<213> ORGANISM: Homo sapiens

<400> SEQUENCE: 15
```

Ala Cys Leu Pro Leu Arg Val Pro Ser Thr Met Arg Ala Trp Ile Phe
1               5                   10                  15

Phe Leu Leu Cys Leu Ala Gly Arg Ala Leu Ala
            20                  25

```
<210> SEQ ID NO 16
<211> LENGTH: 31
<212> TYPE: PRT
<213> ORGANISM: Homo sapiens

<400> SEQUENCE: 16
```

Cys Leu Pro Pro Ala Cys Leu Pro Leu Arg Val Pro Ser Thr Met Arg
1               5                   10                  15

Ala Trp Ile Phe Phe Leu Leu Cys Leu Ala Gly Arg Ala Leu Ala
            20                  25                  30

```
<210> SEQ ID NO 17
<211> LENGTH: 23
<212> TYPE: PRT
<213> ORGANISM: Artificial
<220> FEATURE:
<223> OTHER INFORMATION: B8 scrambled

<400> SEQUENCE: 17
```

Gln Pro Leu Glu Ala Val Gln Pro Thr Ala Val Glu Glu Asp Ala Glu
1               5                   10                  15

Val Glu Thr Thr Glu Glu Val
            20

```
<210> SEQ ID NO 18
<211> LENGTH: 31
```

```
<212> TYPE: PRT
<213> ORGANISM: Artificial
<220> FEATURE:
<223> OTHER INFORMATION: B14 scrambled

<400> SEQUENCE: 18

Val Pro Cys Lys Thr Gly Ser Lys Cys His Asn Asn Asp Pro Pro Thr
1               5                   10                  15

Cys Asn Cys Glu Val Asp Met Cys Leu Gln His Gln Cys Glu His
            20                  25                  30
```

SECRETED PROTEIN ACIDIC AND RICH IN CYSTEINE (SPARC) AS CHEMOTHERAPEUTIC SENSITIZERS

FIELD OF THE INVENTION

The invention relates to cancer therapy sensitizing compositions and methods, specifically polypeptides and polynucleotides relating to the SPARC protein and the SPARC gene.

BACKGROUND OF THE INVENTION

Cancer is one of the leading causes of death in humans and while standard chemotherapy, radiotherapy and surgical intervention successfully reduce tumor load in many cases, resistance to chemotherapeutic intervention is not uncommon, especially in solid tumors. Resistance develops following exposure to chemotherapy and further impedes tumor regression and cure. It is this chemotherapy resistance leading to treatment failure that accounts for the high mortality rates in cancer.

The molecular basis of chemotherapy resistance is largely genetic, and can take many forms. Many mutations responsible for the initial development of tumors may also contribute to drug resistance. For example, loss of DNA mismatch repair (MMR) gene function has been associated with a more rapid emergence of clinical drug resistance in some cancers (de las Alas M. M., et al., 1997. *J Natl Canc Inst* 89:1537-41; Lin X. and Howell, S. B. 1999. *Mol Pharmacol* 56:390-5), and mutations in the K-ras gene (found in approximately 40% of adenomatous polyps and adenocarcinomas) are associated with an increased relapse rate, mortality and a poor chemotherapeutic response (Arber N. et al. 2000. *Gastroenterology* 118:1045-1050). Aberrant expression and dysregulation of proteins involved in the normally tightly regulated cell replication cycle may also be protective of tumors—these proteins may be loosely referred to as 'oncogenes' in the literature. Gene products p21 and p27, for example, have been shown to protect tumors from undergoing apoptosis elicited by various anticancer agents (Waldman T. et al., 1996. Uncoupling of S phase and mistosis induced by anticancer agents in cells lacking p21. *Nature* 381:713 716; St. Croix B. et al., 1996. *Nature Med* 1996, 2:1204-1210). Adhesion molecules, such as E-cadherin, may also confer resistance to cells exposed to chemotherapeutic agents (Skoudy A, et al., 1996. *Biochem J* 317: 279-84.). The mechanisms involved in therapeutic resistance are varied and may be very complex.

Chemosensitizers may act in concert with the chemotherapeutic agent, or may serve to counteract resistance mechanisms in the cell. Existing chemosensitizers include small molecule drugs such as photosensitizers or drug efflux pump inhibitors, and more recently, antisense oligonucleotides. New compounds with chemosensitizing activity include U.S. Pat. No. 5,776,925 and WO 02/00164, which provide examples of novel chemical compounds that enhance cytotoxicity of therapeutic agents.

U.S. Pat. No. 6,001,563 provides for a method for identifying chemical compounds that may have chemosensitizing activity.

Antisense sequences with chemosensitizing activity—often specifically targeting oncogenes—are varied and may be found for almost any target. For example, survivin is a protein that modulates apoptosis and is frequently overexpressed in cancer cells (Krajewska, M. et al. 2003. *Clin Cancer Res* 9:4914; Kaur, P. et al. 2004. *Arch Pathol Lab Med* 128:39; Shariat, S. F. et al., 2004. Urine detection of surviving is a sensitive marker for the noninvasive diagnosis of bladder cancer. *J Urol* 171: 626). Antisense survivin oligonucleotides have been demonstrated to downregulate expression of Survivin, and sensitize cells to chemotherapeutic agents such as docetaxel and etopotide (Hayashi, N. et al., 2005. *Prostate* 15:10-19).

Similarly, cancer therapy sensitizers may act in concert with cancer therapeutic agents, e.g., radiotherapy, or may serve to counteract resistance mechanisms in the cell to the cancer therapeutic agent.

Secreted protein acidic and rich in cysteine (SPARC) is one example of a gene with significantly decreased expression in multidrug resistant cell lines in vitro, with a possible tumor suppressor role (Tai, I. T. et al. 2005. *J. Clin Invest.* 115:1492-1502). SPARC, also known as osteonectin, belongs to a family of matricellular proteins having counter-adhesive properties, disruptive of cell-matrix interactions (Bornstein P. 1995. *J. Cell Biol* 130:503-6; Sage E. H. and Bornstein P. 1991. *J Biol Chem;* 266:14831-4).

SPARC has been demonstrated to play a role in bone mineralization, tissue remodeling, endothelial cell migration, morphogenesis and angiogenesis (Latvala T. et al., 1996. *Exp Eye Res.* 63:579-84; Hasselaar P. and Sage E H. 1992. *J Cell Biochem.* 49:272-83; Mason I. J. et al. 1986. *EMBO J.* 5:1831-7; Strandjord T. P. et al. 1995. *Am J Respir Cell Mol Biol.* 13:279-87; Kupprion C, et al., 1998. *J Biol Chem.* 273: 29635-40; Lane T. F. et al. 1994. *J Cell Biol.* 125:929-43).

Some N-terminal and C-terminal peptides of murine SPARC that block SPARC-mediated anti-spreading activity in bovine aortic endothelial cells in culture are described (Lane T F and Sage, E H 1990. J. Cell Biol 111:3065-3076).

A peptide corresponding to one segment of the follistatin domain inhibits endothelial cell migration in vitro, and angiogenesis in a rat corneal assay model (Chlenski et al 2004. Cancer Res. 64:7420-7425)

Some peptides corresponding to the cationic region of murine SPARC and act as stimulators of capillary growth in vitro and in vivo. However, $Cu^{2+}$ binding activity alone does not appear to be sufficient for a peptide to stimulate angiogenesis (Lane et al 1994. J Cell Biol 125:929-943).

Additional studies suggest that cleavage of SPARC by MMP-3 results in peptides that affect angiogenesis (Sage et al. 2003 J. Biol Chem 287: 37849-37857).

SPARC also has a role in malignancy, as variable gene and protein expression of SPARC have been linked to cancer progression in a number of tumors (Yiu, G. K., et al., 2001. Am J. Pathol 159:609-622; Rempel S. A. et al., 2001. *J Neurooncol* 53:149-60; Schultz C. et al., 2002. *Cancer Res* 62:6270-7; Porter P. L. et al., 1995. *J Histochem Cytochem* 43:791-800). Studies in SPARC knockout animals reveal that loss of SPARC enhances growth of tumor xenografts of pancreatic and lung cancers (Puolakkainen P. A. et al. 2004. *Mol Cancer Res* 2:215-24; Brekken R. A. et al. 2003. *J Clin Invest* 111:487-95).

The use of the intact, isolated SPARC protein as a chemosensitizer is described by WO 2004/064785.

SUMMARY OF THE INVENTION

In accordance with one embodiment of the invention, there is provided an isolated polynucleotide comprising the sequence of SEQ ID NO:2 or SEQ ID NO:4 or SEQ ID NO:6 or SEQ ID NO:11 or SEQ ID NO:12, or an isolated polypeptide comprising the sequence of SEQ ID NO: 3 or SEQ ID NO: 5 or SEQ ID NO:7 or SEQ ID NO:8 or SEQ ID NO:9. In a related embodiment, the invention provides isolated polypeptides, wherein the polypeptides have the amino acid sequence of any of SEQ ID NOs: 3, 5 or 7-10 and up to an additional 50 amino acids, preferably up to an additional 25 amino acids, more preferably up to an additional 15 amino acids, most preferably up to an additional 10 amino acids, wherein the additional amino acids are located at the amino or carboxyl terminus or both termini. The resulting polypeptides, made in accordance with the invention, include polypeptides that are less than 50 amino acids in total length. In a further related embodiment, the invention also provides isolated polynucleotides which encode polypeptides having the amino acid sequence of SEQ ID NOs: 3, 5 and 7-10 with additional amino acids located at the amino or carboxyl terminus or both termini.

In accordance with another embodiment of the invention, there is provided an isolated polypeptide selected from amino acids 17-153 of SEQ ID NO:10, wherein the polypeptide has cancer therapeutic sensitizing activity. In accordance with another embodiment of the invention, there is provided an isolated polynucleotide selected from amino acids 157-56 of SEQ ID NO:10, wherein the polynucleotide has cancer therapeutic sensitizing activity when expressed.

In accordance with another embodiment of the invention, there is provided a medicament comprising SEQ ID NO: 2, SEQ ID NO: 3, SEQ ID NO: 4, SEQ ID NO: 5, SEQ ID NO: 6, SEQ ID NO:7, SEQ ID NO:8, SEQ ID NO:9, SEQ ID NO:10, SEQ ID NO:11 or SEQ ID NO:12. The invention may further comprise a medicament comprising SEQ ID NO: 3 or SEQ ID NO: 5 or SEQ ID NO:7 or SEQ ID NO:8 or SEQ ID NO:9, and a chemotherapeutic agent. The invention may further comprise a medicament comprising both SEQ ID NO: 3 or SEQ ID NO: 5 or SEQ ID NO:7 or SEQ ID NO:8 or SEQ ID NO:9, in combination with a cancer therapeutic agent, including, without limitation, wherein the cancer therapeutic agent is selected from the group consisting of one or more chemotherapeutic agents, one or more radiotherapeutic agents, one or more alternative therapeutic agents, and combinations thereof.

In accordance with another embodiment of the invention, there is provided a vector comprising SEQ ID NO: 2 or SEQ ID NO: 4 or SEQ ID NO: 6 or SEQ ID NO:11 or SEQ ID NO:12, or a host cell expressing a vector comprising SEQ ID NO: 2 or SEQ ID NO:4 or SEQ ID NO:11 or SEQ ID NO:12.

In accordance with another embodiment of the invention, there is provided a method of sensitizing a cancerous cell to a cancer therapeutic regimen, the method comprising; delivery of a vector comprising SEQ ID NO: 2 or SEQ ID NO: 4 or SEQ ID NO: 6 or SEQ ID NO:11 or SEQ ID NO:12, to a cell; expressing the sequence carried by the vector, and; treating the cell with a chemotherapeutic agent. In accordance with a related embodiment of the invention, there is provided a method of sensitizing a cancerous cell to a cancer therapeutic regimen, the method comprises; delivering a polypeptide comprising SEQ ID NO: 3 or SEQ ID NO: 5 or SEQ ID NO:7 or SEQ ID NO:8 or SEQ ID NO:9 to a cell and thereafter treating the cell with a cancer therapeutic agent. These methods of sensitizing cancerous cells may be practiced in accordance with the invention, wherein the cancer therapeutic agent is selected from the group consisting of one or more chemotherapeutic agents, one or more radiotherapeutic agents, one or more alternative therapeutic agents, and combinations thereof.

In accordance with another aspect of the invention, there is provided a polypeptide comprising at least 5 consecutive amino acids of SEQ ID NO: 3 or SEQ ID NO: 5 or SEQ ID NO:7 or SEQ ID NO:8 or SEQ ID NO:9. The polypeptide may further be combined or administered in combination with a medicament comprising a chemotherapeutic agent.

In accordance with another aspect of the invention, there is provided a medicament comprising; a polypeptide comprising at least 5 consecutive amino acids of SEQ ID NO: 3 or SEQ ID NO:5 or SEQ ID NO:7 or SEQ ID NO:8 or SEQ ID NO:9, and a chemotherapeutic agent.

In accordance with another aspect of the invention, there is provided a medicament comprising a polypeptide comprising at least 5 consecutive amino acids of SEQ ID NO: 8 or SEQ ID NO: 9, and a chemotherapeutic agent. The invention may further comprise a medicament comprising both SEQ ID NO: 8 and SEQ ID NO: 9, and a chemotherapeutic agent.

In yet another aspect, the invention provides isolated sensitizing polypeptides comprised of the sequences SEQ ID NOs: 3, 5 and 7-10, wherein one or more amino acids has undergone a conservative mutation. Also provided herein are isolated polynuceotides encoding said conservatively mutated polypeptides.

In accordance with another embodiment of the invention, there is provided a method of sensitizing a cancerous cell to a cancer therapeutic agent, the method including: (a) delivering a polypeptide; selected from one or more of SEQ ID NO: 3, SEQ ID NO: 5, SEQ ID NO:7, SEQ ID NO: 8 and SEQ ID NO: 9; to a cell; and (b) treating the cell with the cancer therapeutic agent.

In accordance with another embodiment of the invention, there is provided a method of sensitizing a cancerous cell to a cancer therapeutic agent, the method including: (a) delivering a vector comprising a polynucleotide selected from one or more of SEQ ID NO: 2, SEQ ID NO: 4, SEQ ID NO:6, SEQ ID NO: 11 and SEQ ID NO: 12; to a cell; (b) expressing the sequence carried by the vector, and (c) treating the cell with a cancer therapeutic agent.

In accordance with another embodiment of the invention, there is provided a vector including an isolated polynucleotide selected from one or more of the following: SEQ ID NO: 2; SEQ ID NO: 4; SEQ ID NO: 6; SEQ ID NO: 11; SEQ ID NO: 12; and fragments, variants, or analogs thereof, wherein the fragments, variants, or analogs thereof retain cancer therapeutic sensitizing activity when expressed.

In accordance with another embodiment of the invention, there is provided a cell including a polynucleotide described herein, wherein the polynucleotide is operably linked to an expression control sequence.

In accordance with another embodiment of the invention, there is provided a cell transfected with the vector as described herein or progeny thereof.

In accordance with another embodiment of the invention, there is provided a method of expressing a polypeptide, including: (a) providing an expression vector encoding the polypeptide, wherein the polypeptide is selected from one or more of the following: SEQ ID NO: 3; SEQ ID NO: 5; SEQ ID NO:7; SEQ ID NO: 8; SEQ ID NO: 9; and fragments, variants, analogs or conservatively mutated polypeptides thereof, wherein the fragments, variants, analogs or conservatively mutated polypeptides thereof retain cancer therapeutic sensitizing activity; (b) introducing the vector into a cell; and (c) maintaining the cell under conditions permitting expression.

The fragments, variants, analogs or conservatively mutated polypeptides thereof, may be determined by one or more of the following: % identity; % similarity; and the degree of conservation as described herein.

The polynucleotide fragments, polynucleotide variants, or polynucleotide analogs thereof, may be determined by one or more of the following: % identity; % similarity; and the ability to hybridize under highly stringent conditions, as described herein.

The delivering and the treating may be simultaneous. The delivering may precede the treating or alternatively, the treating may precede the delivering.

The cancer therapeutic agent may be selected from the group consisting of one or more chemotherapeutic agents, one or more radiotherapeutic agents, one or more alternative therapeutic agents, and combinations thereof.

The polypeptide may be selected from one or more of the following: SEQ ID NO: 3; SEQ ID NO: 5; SEQ ID NO: 7; SEQ ID NO: 8; and SEQ ID NO:9

The polynucleotide may be selected from one or more of the following: SEQ ID NO: 2; SEQ ID NO: 4; SEQ ID NO: 6; SEQ ID NO: 11; and SEQ ID NO: 12.

The cancerous cell may be selected on the basis that it is resistant to a therapeutic regimen. The methods described herein may also comprise a selection step for a cancerous cell that is resistant to a therapeutic regimen.

The isolated polynucleotide may be selected from one or more of the following: SEQ ID NO: 2; SEQ ID NO: 4; SEQ ID NO: 6; SEQ ID NO: 11; SEQ ID NO: 12; and fragments, variants, or analogs thereof, wherein the fragments, variants, or analogs thereof retain cancer therapeutic sensitizing activity when expressed.

The isolated polypeptide may be selected from one or more of the following: SEQ ID NO: 3; SEQ ID NO: 5; SEQ ID NO: 7; SEQ ID NO: 8; SEQ ID NO: 9; and fragments, variants, or analogs thereof, wherein the fragments, variants, or analogs thereof retain cancer therapeutic sensitizing activity. The isolated polypeptide may be selected from one or more of the following: SEQ ID NO: 3; SEQ ID NO: 5; SEQ ID NO: 7; SEQ ID NO: 8; SEQ ID NO: 9; and conservatively mutated polypeptides thereof, wherein the conservatively mutated polypeptides thereof retain cancer therapeutic sensitizing activity.

The isolated polynucleotide may be operably linked to an expression control sequence. The vector may be suitable for gene therapy.

The cell may be operable to express the polypeptides described herein.

The introducing of the vector into a cell may be done in vivo. The introducing of the vector into a cell may be done ex vivo. The introducing of the vector into a cell may be done in vitro.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
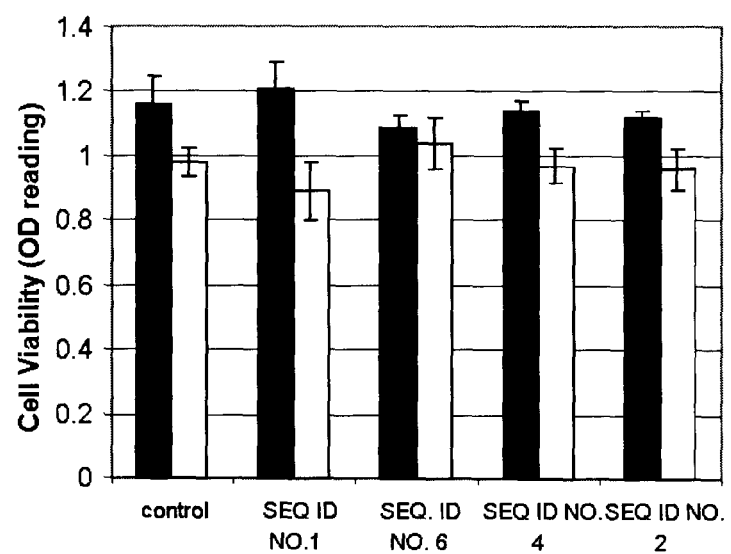
FIG. 1 shows the cell viability assay results from MIP101 cells transiently transfected with a vector expressing full-length SPARC (SEQ ID NO: 1), SEQ ID NO: 2 (N-terminal domain), SEQ ID NO: 4 (follistatin-like domain) OR SEQ ID NO: 6 (EC domain) alone (black bars), or transfected as above, followed by treatment with irinotecan (500 μM) (white bars).

In the description that follows, a number of terms are used extensively, the following definitions are provided to facilitate understanding of the invention.

Current chemotherapy is limited by the ability of the patient to tolerate the drug, and the ability of the cell to resist the cytotoxic effects of the drug. Enhancing or mimicking the enhanced expression of a protein with a tumor suppressive role in the normal cell may avoid the toxicity issues of small molecules, and may have a longer effective half-life when administered to the patient, enabling reduction of the dosage while rendering cancerous cells more susceptible to the chemotherapeutic agent.

As used herein, a "medicament" is a composition capable of producing an effect that may be administered to a patient or test subject. The effect may be chemical, biological or physical, and the patient or test subject may be human, or a non-human animal, such as a rodent or transgenic mouse. The composition may include small organic or inorganic molecules with distinct molecular composition made synthetically, found in nature, or of partial synthetic origin. Included in this group are nucleotides, nucleic acids, amino acids, peptides, polypeptides, proteins, peptide nucleic acids or complexes comprising at least one of these entities. The medicament may be comprised of the effective composition alone or in combination with a pharmaceutically acceptable excipient.

As used herein, a "pharmaceutically acceptable excipient" includes any and all solvents, dispersion media, coatings, antibacterial, antimicrobial or antifungal agents, isotonic and absorption delaying agents, and the like that are physiologically compatible. The excipient may be suitable for intravenous, intraperitoneal, intramuscular, intrathecal or oral administration. The excipient may include sterile aqueous solutions or dispersions for extemporaneous preparation of sterile injectable solutions or dispersion. Use of such media for preparation of medicaments is known in the art.

As used herein, a "pharmacologically effective amount" of a medicament refers to using an amount of a medicament present in such a concentration to result in a therapeutic level of drug delivered over the term that the drug is used. This may be dependent on the mode of delivery, time period of the dosage, age, weight, general health, sex and diet of the subject receiving the medicament. The determination of what dose is a "pharmacologically effective amount" requires routine optimization, which is within the capabilities of one of ordinary skill in the art.

As used herein, the term "cancer" refers to a proliferative disorder caused or characterized by the proliferation of cells which have lost susceptibility to normal growth control. The term cancer, as used in the present application, includes tumors and any other proliferative disorders. Cancers of the same tissue type usually originate in the same tissue, and may be divided into different subtypes based on their biological characteristics. Four general categories of cancers are carcinoma (epithelial tissue derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkins' lymphoma and chronic lymphocyte leukemia. Examples of organs and tissues that may be affected by various cancers include pancreas, breast, thyroid, ovary, uterus, testis, prostate, thyroid, pituitary gland, adrenal gland, kidney, stomach, esophagus, colon or rectum, head and neck, bone, nervous system, skin, blood, nasopharyngeal tissue, lung, urinary tract, cervix, vagina, exocrine glands and endocrine glands. Alternatively, a cancer may be multicentric or of unknown primary site (CUPS).

As used herein, a 'cancerous cell' refers to a cell that has undergone a transformation event and whose growth is no longer regulated to the same extent as before said transformation event. A tumor refers to a collection of cancerous cells, often found as a solid or semi-solid lump in or on the tissue or a patient or test subject.

A cancer or cancerous cell may be described as "sensitive to" or "resistant to" a given therapeutic regimen or chemotherapeutic agent based on the ability of the regimen to kill cancer cells or decrease tumor size, reduce overall cancer growth (i.e. through reduction of angiogenesis), and/or inhibit metastasis. Cancer cells that are resistant to a therapeutic regimen may not respond to the regimen and may continue to proliferate. Cancer cells that are sensitive to a therapeutic regimen may respond to the regimen resulting in cell death, a reduction in tumor size, reduced overall growth (tumor burden) or inhibition of metastasis. For example, this desirably manifest itself in a reduction in tumor size, overall growth/tumor burden or the incidence of metastasis of about 10% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more. Monitoring of a response may be accomplished by numerous pathological, clinical and imaging methods as described herein and known to persons of skill in the art.

A common theme for a chemotherapeutic agent or combination of agents is to induce death of the cancerous cells. For example, DNA adducts such as nitrosoureas, busulfan, thiotepa, chlorambucil, cisplatin, mitomycin, procarbazine, or dacacarbazine slow the growth of the cancerous cell by forcing the replicating cell to repair the damaged DNA before the M-phase of the cell cycle, or may by themselves cause sufficient damage to trigger apoptosis of the cancerous cell. Other events such as gene expression or transcription, protein translation, or methylation of the replicated DNA, for example, may also be interfered with by the varied arsenal of chemotherapeutic agents available to the clinician and help to trigger apoptotic processes within the cancerous cells. Alternately, a chemotherapeutic agent may enable the cancerous cell to be killed by aspects of the patient or test subject's humoral or acquired immune system, for example, the complement cascade or lymphocyte attack.

While not desiring to be bound by any specific theories, a cancerous cell resistant to a chemotherapeutic agent or combination of agents may fight for its survival by actively transporting the drug out of the cell for example, by overexpression of the ABC transporter MDR1 p-glycoprotein (FORD et al 1993. *Cytotechnol.* 12:171-212) or acquiring 'counter-mutations' to counteract the drugs. For example, mutations in the DNA repair enzymes that affect the ability to detect damage to the cells' DNA may enable replication of the damaged DNA and permit the cancerous cells to continue replicating, enlarging the tumor. As mutations accumulate, other regulatory points that would otherwise act in a normal cell cycle cease to function, and the cycle of unregulated growth cascades. Another aspect of chemotherapeutic resistance involves the tumor cells' avoidance of apoptosis. A host organism's normal response to dysregulated cell growth is to initiate apoptosis and eliminate the defective cell before the cascade into uncontrolled replication begins. However, this may be subverted by a cancerous cell, for example, by disruption of signal transduction events, loss of adhesion dependence or contact inhibition in the cancerous cell, or loss of apoptosis-promoting factors, often considered 'tumor suppressors', for example p53, BRCA1 or RB. The importance of this sensitivity to apoptosis in the treatment of cancer is supported by recent evidence indicating that the selectivity of chemotherapy for the relatively few tumors ever cured solely by drugs depends, to a large extent, upon their easy susceptibility to undergo apoptosis (JOHNSTONE et al., 2002. *Cell.* 108(2):153-64).

As used herein, a "therapeutic regimen" or "therapy" refers to the administration of at least one agent which is harmful to cancerous cells. Suitable therapeutic regimens for use in accordance with the invention include, but are not limited to, "chemotherapeutic regimens," "radiotherapeutic regimens," "alternative therapeutic regimen" and combinations thereof.

As used herein, a "chemotherapeutic regimen" or "chemotherapy" refers to the administration of at least one chemotherapy agent which is harmful to destroy cancerous cells. There are a myriad of such chemotherapy agents available to a clinician. Chemotherapy agents may be administered to a subject in a single bolus dose, or may be administered in smaller doses over time. A single chemotherapeutic agent may be used (single-agent therapy) or more than one agent may be used in combination (combination therapy). Chemotherapy may be used alone to treat some types of cancer. Alternatively, chemotherapy may be used in combination with other types of treatment, for example, radiotherapy or alternative therapies (for example immunotherapy) as described herein. Additionally, a chemosensitizer may be administered as a combination therapy with a chemotherapy agent.

As used herein, a "chemotherapeutic agent" refers to a medicament that may be used to treat cancer, and generally has the ability to kill cancerous cells directly. Examples of chemotherapeutic agents include alkylating agents, antimetabolites, natural products, hormones and antagonists, and miscellaneous agents. Examples of alternate names are indicated in brackets. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. Alternate names and trade-names of these and additional examples of chemotherapeutic agents, and their methods of use including dosing and administration regimens, will be known to a person versed in the art, and may be found in, for example "The Pharmacological basis of therapeutics", $10^{th}$ edition. HARDMAN H G., LIMBIRD L E. editors. McGraw-Hill, New York, and in "Clinical Oncology", $3^{rd}$ edition. Churchill Livingstone/Elsevier Press, 2004. ABELOFF, M D. editor. In particular, suitable chemotherapeutic agents for use in accordance with the invention include, without limitation, nanoparticle albumin-bound paclitaxels.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Radiotherapy may further be used in combination chemotherapy, with the chemotherapeutic agent acting as a radiosensitizer. The specific choice of radiotherapy suited to an individual patient may be determined by a skilled person at the point of care, taking into consideration the tissue and stage of the cancer. Examples of radiotherapy approaches to various cancers may be found in, for example "Clinical Oncology", $3^{rd}$ edition. Churchill Livingstone/Elsevier Press, 2004. ABELOFF, M D. editor.

As used herein, the term "alternative therapeutic regimen" or "alternative therapy" may include for example, biologic response modifiers (including polypeptide-, carbohydrate-, and lipid-biologic response modifiers), toxins, lectins, anti-angiogenic agents, receptor tyrosine kinase inhibitors (for example Iressa™ (gefitinib), Tarceva™ (erlotinib), Erbitux™ (cetuximab), imatinib mesilate (Gleevec™), proteosome inhibitors (for example bortezomib, Velcade™); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus, Rapamune™); farnesyltransferase inhibitors (for example tipifarnib, Zarnestra); matrix metalloproteinase inhibitors (for example BAY 12-9566; sulfated polysaccharide tecogalan); angiogenesis inhibitors (for example Avastin™ (bevacizumab); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase kinase inhibitors, Rous sarcoma virus transforming oncogene (SRC) inhibitors, histonedeacetylase inhibitors, small hypoxia-inducible factor inhibitors, hedgehog inhibitors, and TGF-β signalling inhibitors. Furthermore, an immunotherapeutic agent would also be considered an alternative therapeutic regimen. Examples include chemokines, chemotaxins, cytokines, interleukins, or tissue factor. Suitable immunotherapeutic agents also include serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Alternate names and trade-names of these agents used in alternative therapeutic regimens and additional examples of agents used in alternative therapeutic regimens, and their methods of use including dosing and administration regimens, will be known to a physician versed in the art. Furthermore, methods of use of chemotherapeutic agents and other agents used in alternative therapeutic regimens in combination therapies, including dosing and administration regimens, will also be known to a person versed in the art.

In particular, suitable alternative therapeutic regimens include, without limitation, antibodies to molecules on the surface of cancer cells such as antibodies to Her2 (e.g., Trastuzumab), EGF or EGF Receptors, VEGF (e.g., Bevacizumab) or VEGF Receptors, CD20, and the like. The therapeutic agent may further comprise any antibody or antibody fragment which mediates one or more of complement activation, cell mediated cytotoxicity, inducing apoptosis, inducing cell death, and opsinization. For example, such an antibody fragment may be a complete or partial Fc domain.

By "antibodies" it is meant without limitation, monoclonal antibodies, polyclonal antibodies, dimers, multimers, multi-specific antibodies (e.g., bispecific antibodies). Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody.

An antibody includes a full-length immunoglobulin molecule or an immunologically active portion of a full-length immunoglobulin molecule, i.e., a molecule that contains an antigen binding site that immunospecifically binds an antigen of a target of interest or part thereof. Targets include, cancer cells or other cells that produce autoimmune antibodies associated with an autoimmune disease.

The immunoglobulins disclosed herein can be of any class (e.g., IgG, IgE, IgM, IgD, and IgA) or subclass (e.g., IgG1, IgG2, IgG3, IgG4, IgA1 and IgA2) of immunoglobulin molecule. The immunoglobulins can be derived from any species.

"Antibody fragments" comprise a portion of a full length antibody, which maintain the desired biological activity. "Antibody fragments" are generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The monoclonal antibodies referenced herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.γ.RIII only, whereas monocytes express FcγRI, FcγRII and FcγRIII. To assess ADCC activity of a molecule of interest, an in vitro ADCC assay may be performed (U.S. Pat. No. 5,003,621; U.S. Pat. No. 5,821,337). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al PNAS (USA), 95:652-656 (1998).

An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

As used herein, a "chemosensitizer" or "sensitizer" is a medicament that may enhance the therapeutic effect of a chemotherapeutic agent, radiotherapy treatment or alternative therapeutic regimen, and therefore improve efficacy of such treatment or agent. The sensitivity or resistance of a tumor or cancerous cell to treatment may also be measured in an animal, such as a human or rodent, by, e.g., measuring the tumor size, tumor burden or incidence of metastases over a period of time. For example, about 2, about 3, about 4 or about 6 months for a human and about 2-4, about 3-5, or about 4-6 weeks for a mouse. A composition or a method of treatment may sensitize a tumor or cancerous cell's response to a therapeutic treatment if the increase in treatment sensitivity or the reduction in resistance is about 10% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more, compared to treatment sensitivity or resistance in the absence of such composition or method. The determination of sensitivity or resistance to a therapeutic treatment is routine in the art and within the skill of a person versed in the art.

The terms "peptide," "polypeptide," and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties, 2$^{nd}$ ed.*, T. E. Creighton, W H. Freeman and Company, New York, 1993 and Wold F, *Posttranslational Protein Modifications: Perspectives and Prospects*, pgs. 1-12 in *Posttranslational Covalent Modification of Proteins*, B. C. Johnson, ed., Academic Press, New York, 1983; Seifter et al., *Analysis for protein modifications and nonprotein cofactors, Meth. Enzymol.* (1990) 182: 626-646 and Rattan et al. (1992), *Protein Synthesis: Posttranslational Modifications and Aging,"* Ann NY Acad Sci 663: 48-62.

A substantially similar sequence is an amino acid sequence that differs from a reference sequence only by one or more conservative substitutions as discussed herein. Such a sequence may, for example, be functionally homologous to another substantially similar sequence. It will be appreciated by a person of skill in the art the aspects of the individual amino acids in a peptide of the invention that may be substituted.

Amino acid sequence similarity or identity may be computed by, e.g., using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

Sequences on which to perform an alignment may be collected from numerous databases. Examples of protein databases include SWISS-PROT, which also provides a high level of annotation relating to the function of a protein, its domains structure, post-translational modifications, variants (Bairoch A. and Apweiler R. (2000) Nucleic Acids Res. 28(1):45-48; Bairoch A. and Apweiler R. (1997) J. Mol. Med. 75(5):312-316; Junker V. L. et al. (1999) Bioinformatics 15(12):1066-1007), TrEMBL a computer-annotated supplement of SWISS-PROT that contains all the translations of EMBL nucleotide sequence entries (Bairoch A. and Apweiler R. (2000) Nucleic Acids Res. 28(1):45-48) and nr database compares all non-redundant GenBank CDS translations plus protein sequences from other databases such as PDB, SwissProt, PIR and PRF.

Alignments of protein sequences may be conducted using existing algorithms to search databases for sequences similar to a query sequence. One alignment method is the Smith-Waterman algorithm (Smith, T. F. and Watermane, M. S. 1981. Journal of Molecular Biology 147(1):195-197), which is useful in determining how an optimal alignment between the query sequence and a database sequence can be produced. Such an alignment is obtained by determining what transformations the query sequence would need to undergo to match the database sequence. Transformations include substituting one character for another and inserting or deleting a string of characters. A score is assigned for each character-to-character comparison-positive scores for exact matches and some substitutions, negative scores for other substitutions and insertions/deletions. Scores are obtained from statistically-derived scoring matrices. The combination of transformations that results in the highest score is used to generate an alignment between the query sequence and database sequence. The Needleman-Wunsch (Needleman, S. B. and Wunsch, C. D. 1970. Journal of Molecular Biology 48(3):443-453) algorithm is similar to the Smith-Waterman algorithm, but sequence comparisons are global, not local. Global comparisons force an alignment of the entire query sequence against the entire database sequence. While local alignments always begin and end with a match, global alignments may begin or end with an insertion or deletion (indel). For a given query sequence and database sequence, a global score will be less than or equal to a local score due to indels on the ends. As an alternative to the above algorithms, a Hidden Markov Model (HMM) search (Eddy, S. R. 1996. Current Opinion in Structural Biology 6(3):361-365) could be used to generate protein sequence alignments. HMM scoring weighs the probability of a match being followed by insertions/deletions or vice-versa. In addition, HMMs allow insertion to deletion transitions (and vice versa) and scoring of begin and end states to control whether a search is run globally or locally.

One or more of the above algorithms may be used in an alignment program to generate protein sequence alignments. A person skilled in the art has numerous sequence alignment programs to choose from, that incorporate a variety of different algorithms. One example of an alignment program is BLASTP (Altschul, S. F., et al. (1997) Nucleic Acids Res. 25(17):3389-3402). Other alignment programs are CLUSTAL W and PILEUP. The standard output from a BLASTP run contains enough information to conduct further indel analysis as described below.

Amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic.

Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance with the following Table 1:

TABLE 1

Nomenclature and abbreviations of the 20 standard L-amino acids commonly found in naturally occurring peptides.

| Full name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. *J Mol Biol* 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4.2). Amino acids with similar hydropathy indices may be substitutable for each other in a peptide.

Amino acids comprising the peptides described herein will be understood to be in the L- or D-configuration. In peptides and peptidomimetics of the present invention, D-amino acids may be substitutable for L-amino acids.

Amino acids contained within the peptides of the present invention, and particularly at the carboxy- or amino-terminus, may be modified by methylation, amidation, acetylation or substitution with other chemical groups which may change the circulating half-life of the peptide without adversely affecting their biological activity. Additionally, a disulfide linkage may be present or absent in the peptides of the invention.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and nonstandard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

In order to further exemplify what is meant by a conservative amino acid substitution, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, iso-butyl, —CH$_2$CH$_2$OH, —CH$_2$CH$_2$CH$_2$OH, —CH$_2$CHOHCH$_3$ and CH$_2$SCH$_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —(CH2)3COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruline, 2-amino guanidinobutanoic acid, homologs of lysine, homologs of arginine, and ornithine.

Group F includes serine, threonine, cysteine, and modified amino acids having C1-C5 straight or branched alkyl side chains substituted with —OH or —SH.

Groups A-F are exemplary and are not intended to limit the invention.

A peptidomimetic is a compound comprising non-peptidic structural elements that mimics the biological action of a parent peptide. A peptidomimetic may not have classical peptide characteristics such as an enzymatically scissile peptidic bond. A parent peptide may initially be identified as a binding sequence or phosphorylation site on a protein of interest, or may be a naturally occurring peptide, for example a peptide hormone. Assays to identify peptidomimetics may include a parent peptide as a positive control for comparison purposes, when screening a library, such as a peptidomimetic library. A peptidomimetic library is a library of compounds that may have biological activity similar to that of a parent peptide.

As used herein, the term "polynucleotide" includes RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

"Peptide nucleic acids" (PNA) as used herein refer to modified nucleic acids in which the sugar phosphate skeleton of a nucleic acid has been converted to an N-(2-aminoethyl)-glycine skeleton. Although the sugar-phosphate skeletons of DNA/RNA are subjected to a negative charge under neutral conditions resulting in electrostatic repulsion between complementary chains, the backbone structure of PNA does not inherently have a charge. Therefore, there is no electrostatic repulsion. Consequently, PNA has a higher ability to form double strands as compared with conventional nucleic acids, and has a high ability to recognize base sequences. Furthermore, PNAs are generally more robust than nucleic acids. PNAs may also be used in arrays and in other hybridization or other reactions as described above and herein for oligonucleotides.

As used herein, the term "vector" refers to a polynucleotide compound used for introducing exogenous or endogenous polynucleotide into host cells. A vector comprises a nucleotide sequence, which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

As used herein, a "tumor suppressor" is a gene or gene product that has a normal biological role of restraining unregulated growth of a cell. If the function of a tumor suppressor is lost, unregulated cell growth arises. The functional counterpart to a tumor suppressor is an oncogene—genes that promote normal cell growth may be known as 'protooncogenes'. A mutation that activates such a gene or gene product further converts it to an 'oncogene', which continues the cell growth activity, but in a dysregulated manner. Examples of tumor suppressor genes and gene products are well known in the literature and may include PTC, BRCA1, BRCA2, p16, APC, RB, WT1, EXT1, p53, NF1, TSC2, NF2, VHL or SPARC. Further examples of tumor suppressor genes, gene products and their functions may be found in: McKusick, V. A.: *Mendelian Inheritance in Man. A Catalog of Human Genes and Genetic Disorders*. Baltimore: Johns Hopkins University Press, 1998 (12th edition), and in the online companion site: Online Mendelian Inheritance in Man, OMIM (™). McKusick-Nathans Institute for Genetic Medicine, Johns Hopkins University (Baltimore, Md.) and National Center for Biotechnology Information, National Library of Medicine (Bethesda, Md.), 2000. World Wide Web URL: http://www.ncbi.nlm.nih.gov/omim/.

The invention further provides nucleic acid constructs comprising control elements and a nucleic acid molecule described herein operatively linked to the control elements (e.g., a suitable promoter) for expression of a polypeptide or a polypeptide herein described. Protein expression is dependent on the level of RNA transcription, which is in turn regulated by DNA signals. Similarly, translation of mRNA requires, at the very least, an AUG initiation codon, which is usually located within about 10 to about 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, J. Molec. Biol. 196: 947-950 (1987)). Also, successful expression of an exogenous nucleic acid in a cell can require post-translational modification of a resultant protein. Accordingly, the invention provides plasmids encoding polypeptides wherein the vector is, e.g., pCDNA3.1 or a derivative thereof.

The nucleic acid molecules described herein preferably comprise a coding region operatively linked to a suitable promoter, which promoter is preferably functional in eukaryotic cells. Viral promoters, such as, without limitation, the RSV promoter and the adenovirus major late promoter can be used in the invention. Suitable non-viral promoters include, but are not limited to, the phosphoglycerokinase (PGK) promoter and the elongation factor 1α promoter. Non-viral promoters are desirably human promoters. Additional suitable genetic elements, many of which are known in the art, also can be ligated to, attached to, or inserted into the inventive nucleic acid and constructs to provide additional functions, level of expression, or pattern of expression. The native promoters for expression of the SPARC family genes also can be used, in which event they are preferably not used in the chromosome naturally encoding them unless modified by a process that substantially changes that chromosome. Such substantially changed chromosomes can include chromosomes transfected and altered by a retroviral vector or similar process. Alternatively, such substantially changed chromosomes can comprise an artificial chromosome such as a HAC, YAC, or BAC.

In addition, the nucleic acid molecules described herein may be operatively linked to enhancers to facilitate transcription. Enhancers are cis-acting elements of DNA that stimulate the transcription of adjacent genes. Examples of enhancers which confer a high level of transcription on linked genes in a number of different cell types from many species include, without limitation, the enhancers from SV40 and the RSV-LTR. Such enhancers can be combined with other enhancers which have cell type-specific effects, or any enhancer may be used alone.

To optimize protein production the inventive nucleic acid molecule can further comprise a polyadenylation site following the coding region of the nucleic acid molecule. Also, preferably all the proper transcription signals (and translation signals, where appropriate) will be correctly arranged such that the exogenous nucleic acid will be properly expressed in the cells into which it is introduced. If desired, the exogenous nucleic acid also can incorporate splice sites (i.e., splice acceptor and splice donor sites) to facilitate MRNA production while maintaining an inframe, full length transcript. Moreover, the inventive nucleic acid molecules can further comprise the appropriate sequences for processing, secretion, intracellular localization, and the like.

The nucleic acid molecules can be inserted into any suitable vector. Suitable vectors include, without limitation, viral vectors. Suitable viral vectors include, without limitation, retroviral vectors, alphaviral, vaccinial, adenoviral, adenoassociated viral, herpes viral, and fowl pox viral vectors. The vectors preferably have a native or engineered capacity to transform eukaryotic cells, e.g., CHO-K1 cells. Additionally, the vectors useful in the context of the invention can be "naked" nucleic acid vectors (i.e., vectors having little or no proteins, sugars, and/or lipids encapsulating them) such as plasmids or episomes, or the vectors can be complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules.

One measure of "correspondence" of nucleic acids, peptides or proteins for use herein with reference to the above described nucleic acids and proteins is relative "identity" between sequences. In the case of peptides or proteins, or in the case of nucleic acids defined according to a encoded peptide or protein correspondence includes a peptide having at least about 50% identity, alternatively at least about 70% identity, alternatively at least about 90% identity, or even about 95% and may also be at least about 98-99% identity to a specified peptide or protein. Preferred measures of identity as between nucleic acids is the same as specified above for peptides with at least about 90% or at least about 98-99% identity being most preferred.

The term "identity" as used herein refers to the measure of the identity of sequence between two peptides or between two nucleic acids molecules. Identity can be determined by comparing a position in each sequence, which may be a line for purposes of comparison. Two amino acid or nucleic acid sequences are considered substantially identical if they share at least about 75% sequence identity, preferably at least about 90% sequence identity and even more preferably at least 95% sequence identity and most preferably at least about 98-99% identity.

Sequence identity may be determined by the BLAST algorithm currently is use and which was originally described in Altschul et al. (1990) J. Mol. Biol. 215:403-410. The BLAST algorithm may be used with the published default settings. When a position in the compared sequence is occupied by the same base or amino acid, the molecules are considered to have shared identity at that position. The degree of identity between sequences is a function of the number of matching positions shared by the sequences.

An alternate measure of identity of nucleic acid sequences is to determine whether two sequences hybridize to each other under low stringency, and preferably high stringency conditions. Such sequences are substantially identical when they will hybridize under high stringency conditions. Hybridization to filter-bound sequences under low stringency conditions may, for example, be performed in 0.5 M $NaHPO_4$, 7% sodium dodecyl sulfate (SDS), 1 mM EDTA at 65° C., and washing in 0.2×SSC/0.1 SDS at 42° C. (see Ausubel et al. (eds.) 1989, *Current Protocols in Molecular Biology, Vol.* 1, Green Publishing Associates, Inc., and John Wiley & sons, Inc., New York, at p. 2.10.3). Alternatively, hybridization to filter-bound sequences under high stringency conditions, may for example, be performed in 0.5 M $NaHPO_4$, 7% (SDS), 1 mM EDTA at 65° C., and washing in 0.2×SSC/0.1% SDS at 68° C. (see Ausubel et al. (eds.) 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of Principles in Hybridization and the Strategy of Nucleic Acid Probe Assays", Elsevier, N.Y.). Generally, stringent conditions are selected to be about 5° C. lower than the thermal melting point for the specific sequence at a defined ionic strength and pH.

The full-length SPARC protein has multiple functional domains, including an N-terminal acidic domain, a follistatin-like domain that may inhibit cell proliferation and a C-terminal extracellular domain that binds calcium ions with high affinity and inhibits cell proliferation. When the full-length SPARC protein is administered to a mouse tumour model, chemosensitizing activity has been demonstrated, improving the response rate of resistant tumours to chemotherapeutic agents, for example 5-fluorouracil, irinotecan, cisplatin or etoposide.

Which of these domains, or regions within these domains, are responsible for the apoptotic-mediating or chemosensitizing effects of SPARC have not been previously investigated.

It will be appreciated by a person of skill in the art that the numerical designations of the positions of mutations within a sequence are relative to the specific sequence. Also the same positions may be assigned different numerical designations depending on the way in which the sequence is numbered and the sequence chosen. Furthermore, sequence variations such as insertions or deletions, may change the relative position and subsequently the numerical designations of particular nucleotides at and around a mutational site.

SEQ ID NO: 1 (NM_003118) is the full-length cDNA sequence encoding the SPARC protein. When translated, the 303 amino acid SPARC protein is produced (SEQ ID NO: 10). SEQ ID NO: 2 consists of nucleotides 157-309 of the SPARC cDNA. These nucleotides correspond to the N-terminal acidic domain of the SPARC protein (NT)—amino acids 17-68 (SEQ ID NO: 3). SEQ ID NO: 4 consists of nucleotides 310-565 of the SPARC cDNA. These nucleotides correspond to the follistatin-like domain of the SPARC protein (FS)—amino acids 69-153 (SEQ ID NO: 5). SEQ ID NO: 6 consists of nucleotides 566-1015 of the SPARC cDNA. These nucleotides correspond to the extracellular domain of the SPARC protein (EC)—amino acids 154-303 (SEQ ID NO: 7). SEQ ID NO: 11 consists of nucleotides 157-225 of the SPARC cDNA. These nucleotides correspond to the B8 peptide (SEQ ID NO: 8). SEQ ID NO: 12 consists of nucleotides 319-411 of the SPARC cDNA. These nucleotides correspond to the B14 peptide (SEQ ID NO: 9). Additional peptide sequences corresponding to the first 17 amino acids of the full length SPARC protein or the first 17 amino acids with additional amino acid residues at the N-terminus of the peptide are identified as follows: A (SEQ ID NO: 13); A1 (SEQ ID NO: 14); A2 (SEQ ID NO: 15); and A3 (SEQ ID NO: 16). Furthermore, peptides B8 and B14 were scrambled to produce negative control peptides B8-SCR (SEQ ID NO: 17), and B14-SCR (SEQ ID NO: 18).

Figure 2:
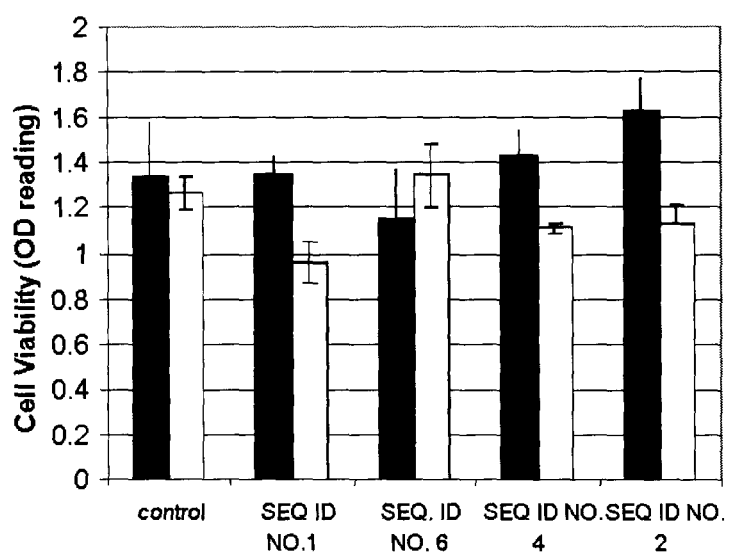
FIG. 2 shows the cell viability assay results from MIP/CPT (CPT-11 resistant) cells transiently transfected with a vector expressing full-length SPARC (SEQ ID NO: 1), SEQ ID NO: 2 (N-terminal domain), SEQ ID NO: 4 (follistatin-like domain) OR SEQ ID NO: 6 (EC domain) alone (black bars), or transfected as above, followed by treatment with irinotecan (500 μM) (white bars).

Transfection of vectors expressing polynucleotide fragments (SEQ ID NO: 2 and SEQ ID NO: 4) of SPARC into sensitive and resistant tumor cell lines indicated that the follistatin-like region (encoded by the polynucleotide sequence SEQ ID NO: 4, translated to polypeptide sequence SEQ ID NO:5) and the immediate N-terminal region including an uncleaved signal sequence (encoded by the polynucleotide sequence SEQ ID NO: 2, translated to polypeptide sequence SEQ ID NO:3) are similarly capable of inducing apoptosis in vitro when concomitantly subjected to a chemotherapeutic agent (FIGS. 1 and 2). The follistatin-like region interacts with an EC domain to bind calcium, and may control calcium homeostasis—a key factor in apoptosis regulation. Overexpression of these polypeptides may interfere with protein-protein interactions involving cellular proteins that, in non-cancerous cells, may interact with SPARC and stimulate apoptosis.

Gene therapy is a medical intervention that involves modifying the genetic material of living cells to fight disease. Gene therapy is being studied in clinical trials (research studies with humans) for many different types of cancer and for other diseases. Accordingly, the invention further provides for an isolated nucleic acid molecule encoding a SPARC polypeptide suitable for use in "gene therapy" (see, e.g., Patil et al., AAPS J. 7(1):E61-77 (2005)).

In general, a gene is delivered to the cell using a "vector" such as those disclosed herein. The most common types of vectors used in gene therapy are viruses. Viruses used as vectors in gene therapy are genetically disabled; they are unable to reproduce themselves. Most gene therapy clinical trials rely on mouse retroviruses to deliver the desired gene. Other viruses used as vectors include adenoviruses, adeno-associated viruses, poxviruses, and the herpes virus. Suitable viral gene therapy vectors and modes of their administration in vivo and ex vivo are known in the art.

Gene therapy can be performed both ex vivo and in vivo. Typically, in ex vivo gene therapy clinical trials, cells from the patient's blood or bone marrow are removed and grown in the laboratory. The cells are exposed to the virus that is carrying the desired gene. The virus enters the cells, and the desired gene becomes part of the cells' DNA. The cells grow in the laboratory and are then returned to the patient by injection into a vein. Using in vivo gene therapy, vectors such as, e.g., viruses or liposomes may be used to deliver the desired gene to cells inside the patient's body.

Identification of key SPARC polypeptide sequences involved in control of apoptosis precedes the development of peptide-based chemosensitizing therapeutics to be used in conjunction with chemotherapeutic agents. Individual synthetic polypeptides spanning at least 5 consecutive amino acids of the N-terminal third of SPARC, including the cleaved secretion signal sequence in the immature SPARC, may, in combination with a chemotherapeutic agent, serve to sensitize the cancerous cells in a resistant tumor. Assays to identify suitable synthetic polypeptides may be performed by exposing resistant cancerous cells in vitro or in vivo to at least one isolated polypeptide and a chemotherapeutic agent (alone or in combination), followed by continued exposure to a chemotherapeutic agent as described herein. Cell survival and apoptosis may be assessed using methods described herein.

Peptides according to one embodiment of the invention may include peptides comprising the amino acid sequences provided in Table 2. Other peptides according to other embodiments of the invention may include peptides having a substantially similar sequence to those provided in Table 2. Such peptides may be in isolation, or may be linked to or in combination with tracer compounds, protein translocation sequences, liposomes, carbohydrate carriers, polymeric carriers or other agents or excipients as will be apparent to one of skill in the art. In an alternate embodiment, such peptides may comprise a medicament, wherein such peptides may be present in a pharmacologically effective amount.

The present invention provides compositions and methods for sensitizing cancer therapeutic treatments. Such sensitizing compositions and methods are particularly useful in enhancing the response of patients who are resistant to a treatment. They are also useful in reducing the side-effects of cancer therapy, for example, by enhancing the response of a patient to a smaller strength (i.e., dosage) of the treatment. The composition of the present invention may reduce the dosage of a therapeutic treatment agent by at least about 10%, for example, at least about 30%, at least about 40%, at least about 50%, and at least about 60%.

TABLE 3

Peptide sequences

| SEQ ID NO. | Peptide name | Amino Acid Sequence (N to C) | Chemo-sensitizer (Y/N) |
|---|---|---|---|
| 3 | NT | APQQEALPDETEVVEETVAEVTEVSVG ANPVQVEVGEFDDGAEETEEEVVA | Y |
| 5 | FS | ENPCQNHHCKHGKVCELDENNTPMCVC QDPTSCPAPIGEFEKVCSNDNKTFDSS CHFFATKCTLEGTKKGHKLHLDYIGPC KYIP | Y |
| 7 | EC | CLDSELTEFPLRMRDWLKNVLVTLYER DEDNNLLTEKQKLRVKKIHENEKRLEA GDHPVELLARDFEKNYNMYIFPVHWQF GQLDQHPIDGYLSHTELAPLRAPLIPM EHCTTRFFETCDLDNDKYIALDEWAGC FGIKQKDIDKDLVI | Y |
| 8 | B8 | APQQEALPDETEVVEETVAEVTE | Y |
| 9 | B14 | CQNHHCKHGKVCELDENNTPMCVCQDP TSCP | Y |
| 13 | A | ESALCLPPACLPLRVPSTMRAWLFFLL CLAGRALA | N |
| 14 | A1 | MRAWIFFLLCLAGRALA | N |
| 15 | A2 | ACLPLRVPSTMRAWIFFLLCLAGRALA | N |
| 16 | A3 | CLPPACLPLRVPSTMRAWIFFLLCLAG RALA | N |
| 17 | B8-SCR | QPLEAVQPTAVEEDAEVETTEEV | N |
| 18 | B14-SCR | VPCKTGSKCHNNDPPTCNCEVDMCLQH QCEH | N |

SCR = scrambled peptide

Those of ordinary skill in the art will recognize that, because of the universality of the genetic code, the knowledge of any given amino acid sequence allows those of ordinary skill in the art to readily envision a finite number of specific polynucleotide sequences that can encode a polypeptide of said amino acid sequence. Further, the ordinarily skilled artisan can readily determine the optimal polynucleotide sequence to encode a polypeptide of said amino acid sequence for expression in any given species via the process of "codon optimization," which is well know in the art (see, e.g., VILLALOBOS et al.: Gene Designer: a synthetic biology tool for constructing artificial DNA segments. BMC Bioinformatics. 2006 Jun. 6; 7:285).

The present invention provides, in one embodiment, a composition comprising a SPARC polypeptide and a chemotherapy-resistant cell. In addition to sensitizing a sample or a mammal to cancer therapy, the use of the subject compositions of the present invention can reduce the dosage of a therapy, therefore reducing the side effects caused by cancer therapy. The above compositions may comprise a pharmaceutical composition, which further includes a pharmaceutically acceptable carrier or excipient.

As used herein, a "carrier" refers to any substance suitable as a vehicle for delivering an Active Pharmaceutical Ingredient (API) to a suitable in vitro or in vivo site of action. As such, carriers can act as an excipient for formulation of a therapeutic or experimental reagent containing an API. Preferred carriers are capable of maintaining an API in a form that is capable of interacting with a T cell. Examples of such carriers include, but are not limited to water, phosphate buffered saline, saline, Ringer's solution, dextrose solution, serum-containing solutions, Hank's solution and other aqueous physiologically balanced solutions or cell culture medium. Aqueous carriers MAY also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer.

Methods

Cloning and Plasmid Construction

Polynucleotide fragments corresponding to SEQ ID NO: 2, SEQ ID NO: 4 or SEQ ID NO: 6 were amplified by PCR and inserted into the pSecTag vector (Invitrogen), and verified by sequencing.

Cell Culture and Maintenance

Colorectal cell lines MIP101 and MIP/CPT cells were maintained in Dulbecco's modified Eagle's medium (DMEM) (Invitrogen) supplemented with 10% fetal bovine serum (FBS) (Invitrogen), 1% penicillin/streptomycin (Invitrogen) at 37° C. and 5% $CO_2$.

Development of Resistant Cell Lines

Resistant MIP101 cells were developed following long-term incubation with incremental concentrations of 5 fluorouracil (5-FU) (10-500 uM), irinotecan (CPT) (1-50 uM; Pharmacia), cisplatin (CIS) (1-100 uM) or etoposide (ETO) (0.1-5 uM: Sigma-Aldrich). The concentration of each agent was increased 10% every 2 weeks for a 6 month period.

Transient Transfection

Transient transfections were performed as previously described (Tai TC et al., 2001. *J Neurochem;* 76:1851-9) Briefly, MIP 101 colorectal cancer cells and resistant MIP/CPT cells grown to 50-60% confluency in 96-well tissue culture plates were transfected with 1.0 µg of vector (control) or vector+SPARC fragments using PEI transfection (Tai, T. C. et al., 2002. *Mol Pharmacol* 61:1385-92). After transfection, cells were washed with DMEM medium (supplemented with 10% FBS, 1% penicillin/streptomycin) and incubated in fresh media for 48 hrs prior to incubation with chemotherapeutic agents (5-FU 1000 µM or CPT-11 500 µM) for 24 hrs. Cell proliferation was assessed by MTS assay (Promega).

Peptide Assays

Sensitive MIP 101 and resistant MIP/5FU cells were seeded at a density of 8,000 cells/well (96-well plate) in DMEM supplemented with 10% FBS, 1% penicillin/streptomycin. After incubation at 37° C. with 5% $CO_2$ for 48 hrs, the media was removed and fresh serum-free conditioned medium (VP-SFM, Invitrogen) containing the peptide of interest was incubated for an additional 48 hrs in the presence or absence of 500 µM 5-FU. Cell viability was assessed by MTS assay.

Peptides were custom synthesized by Sigma. Peptides A, A1, A2, A3 were dissolved in 0.1% DMSO. Peptides B8, B14, B8-scramble and B14-scramble were dissolved in PBS. For the MTS cell viability assay, a dose response curve was obtained using a "high" peptide concentration of 200 µg/ml, and a "low" peptide concentration of 96 µm/ml.

Cell Viability (MTS Assay)

For the MTS assay, 3-(4,5-dimethylthiazol-2-yl)-5-(3-carboxy-methoxyphenyl)-2-(4-sulfophenyl)-2H-tetrazolium inner salt (MTS) and phenazine methosulfate (PMS), purchased from Promega (Madison, Wis.), were mixed in the proportions 2:0.92 µg/ml, and 25 µl of the mixture was added to each well. After incubation at 37° C. with 5% $CO_2$ for 2 h, the absorbance of each well at 490 nm was measured in a 96-well plate reader (Versa Max, version 4.8, Molecular Devices Co.) according to the manufacturer's instructions. Cell viability was expressed as a percentage of control.

Statistical difference between groups was determined by analysis of variance followed by post hoc comparison with Student's t-test. A P-value<0.05 was considered statistically significant

EXAMPLES

Example 1

Sensitive (MIP101—FIG. 1) and multi-drug resistant (MIP/CPT—FIG. 2) cells were transiently transfected and assayed for survival upon exposure to irinotecan (CPT). Cell viability was quantified by an MTS assay. Transfection of both SEQ ID NO: 2 and SEQ ID NO: 4 had a similar effect by decreasing cell viability in the resistant MIP/CPT cells compared to that of the full length SPARC vector. Resistant MIP/CPT cells transfected with control (empty vector) remained viable despite exposure to 500 uM CPT-11.

Example 2

Use of SPARC Peptide Chemosensitizers In Vitro

This example demonstrates the utility of the inventive SPARC peptide chemosensitizers in an in vitro model system.

Shorter peptides corresponding to various regions of either the N-terminal acidic region or the follistatin domain were synthesized to further narrow the peptide sequences demonstrating chemosensitizing activity.

Figure 4:
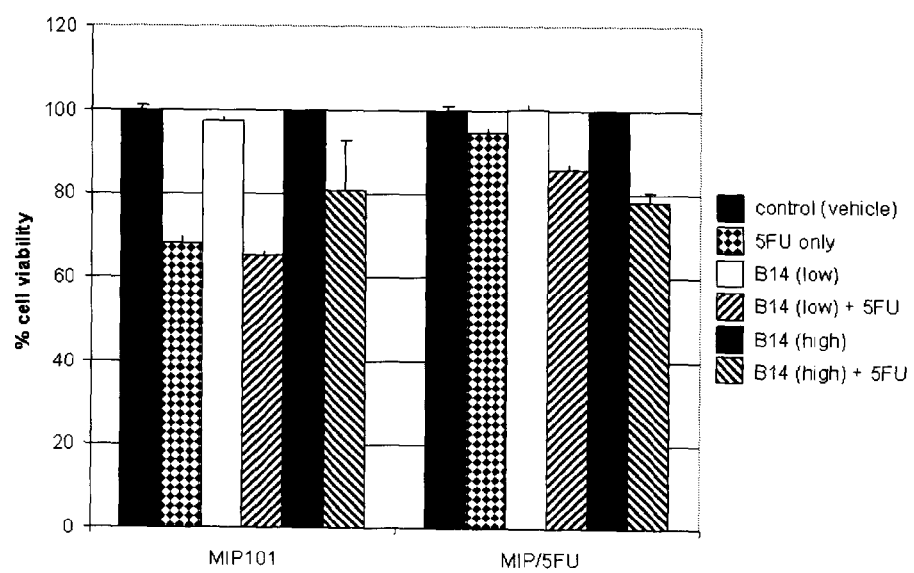
FIG. 4 shows cell viability results from MIP (5FU sensitive) and MIP/5FU (5FU resistant) cells exposed to the B14 peptide at low (96 μg/ml) and high (200 μm/ml) concentrations, alone or in combination with 5FU (500 μM).

MIP101 sensitive or resistant to 5-FU (MIP/5FU) cells were exposed to the B14 peptide (SEQ ID NO. 9) as described. In both resistant and sensitive cells, the peptide alone, at either of the concentrations tested did not significantly affect viability (FIG. 4). As expected the resistant cells exhibited greater viability in the presence of 5-FU alone— with the addition of the B14 peptide at 96 or 200 µg/ml, cell viability decreased compared to 5-FU alone, indicating that the presence of the peptide increases the sensitivity of the resistant cells to the chemotherapeutic agent.

Figure 3:
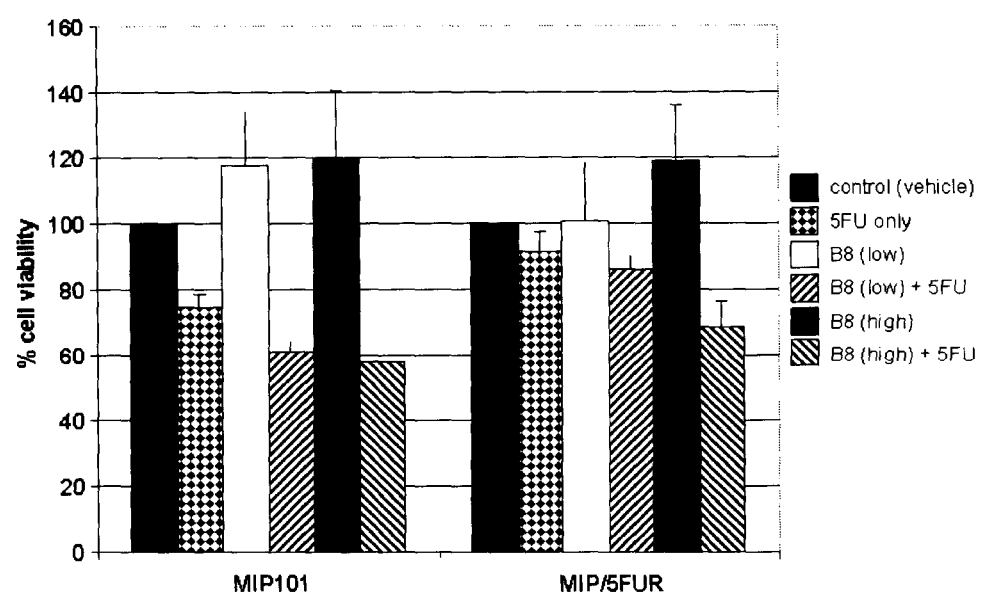
FIG. 3 shows cell viability results from MIP (5FU sensitive) and MIP/5FU (5FU resistant) cells exposed to the B8 peptide at low (96 μg/ml) and high (200 μg/ml) concentrations, alone or in combination with 5FU (500 μM).

A similar trend is observed when the MIP101 cells sensitive or resistant to 5-FU (MIP/5FU) were exposed to the B8 peptide (SEQ ID NO.8) (FIG. 3). The peptide alone, at either concentration did not affect cell viability. In the resistant cells (MIP/5FU), the drug by itself had no effect on cell viability, but in the presence of increasing concentrations of peptide, there was increasing sensitivity of the resistant cells to the chemotherapeutic agent.

Figure 5:
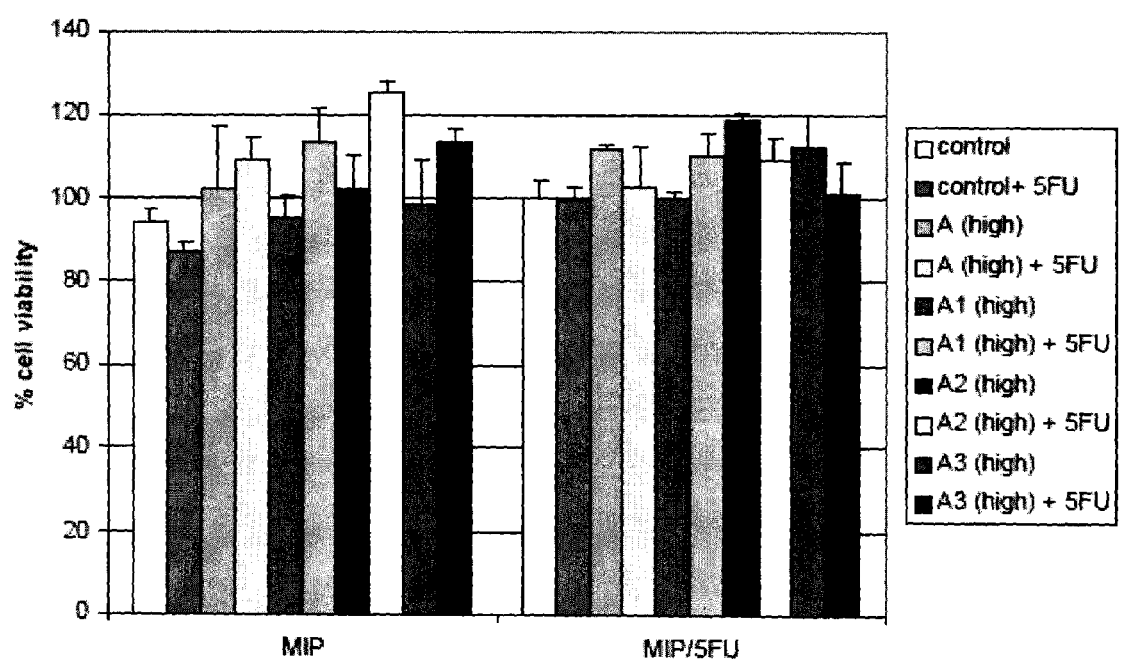
FIG. 5 shows cell viability results from MIP (5FU sensitive) and MIP/5FU (5FU resistant) cells exposed to the A, A1, A2 and A3 peptides at high (200 μg/ml) concentrations, alone or in combination with 5FU (500 μM).
Figure 6:
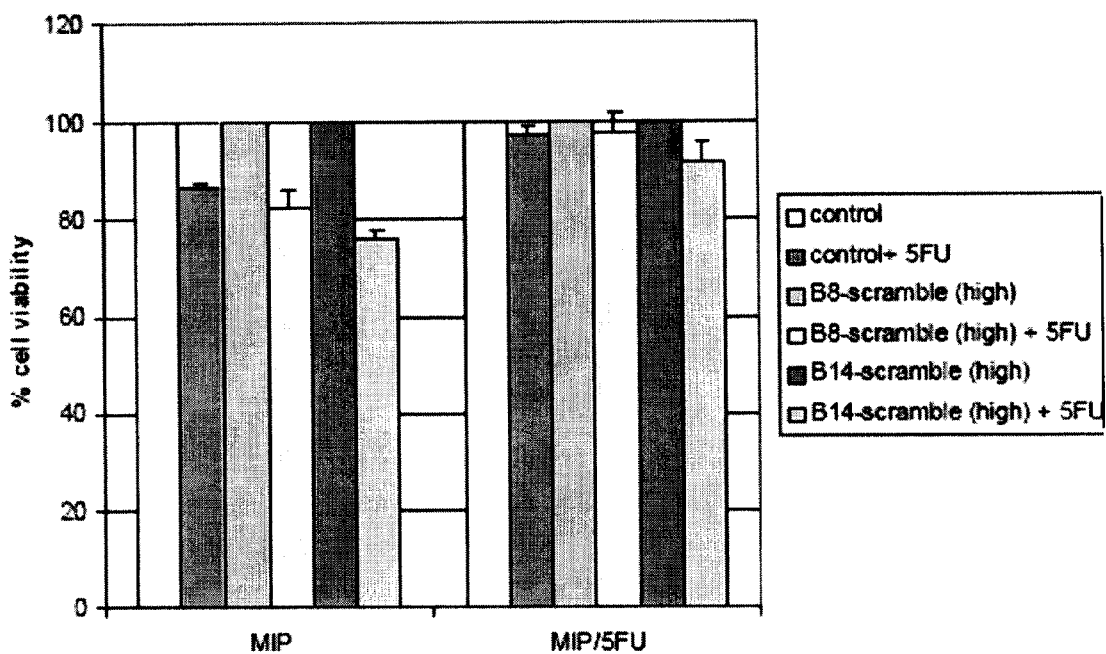
FIG. 6 shows cell viability results from MIP (5FU sensitive) and MIP/5FU (5FU resistant) cells exposed to the B8-scramble and B14-scramble peptides at high (200 μm/ml) concentrations, alone or in combination with 5FU (500 μM).
Figure 7:
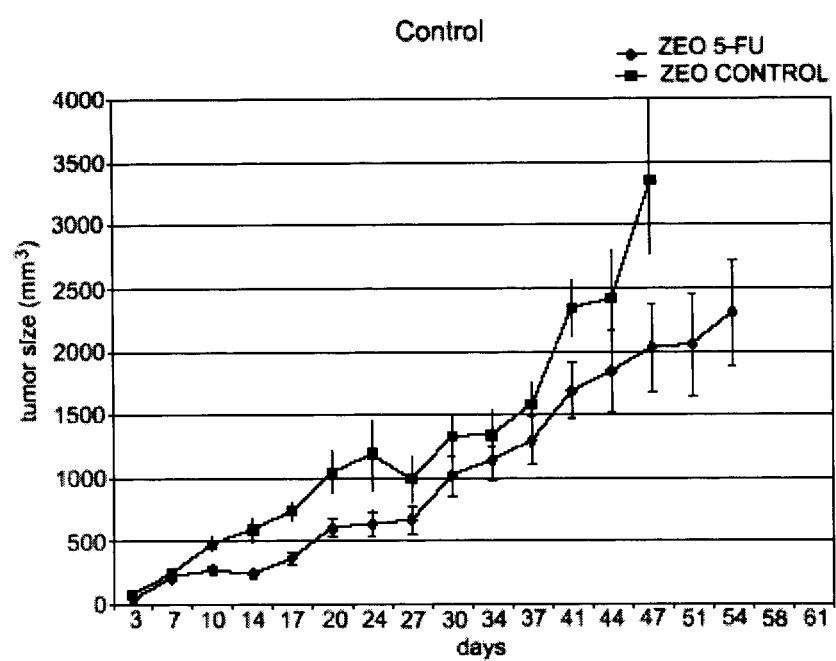
FIG. 7 shows the results of in vivo sensitization to the chemotherapeutic agent 5-FU as measured by tumor growth in a xenograft system comprising transplanted control tumor cells (growth with and without 5-FU).
Figure 8:
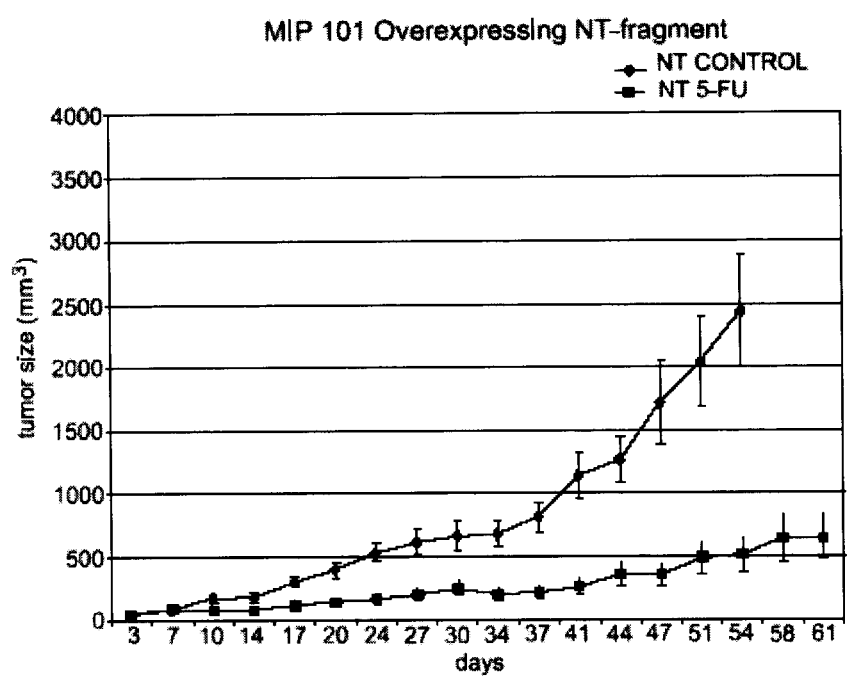
FIG. 8 shows the results of in vivo sensitization to the chemotherapeutic agent 5-FU as measured by tumor growth in a xenograft system comprising transplanted tumor cells expressing SEQ ID NO: 2/NT-Fragment (growth with and without 5-FU).
Figure 9:
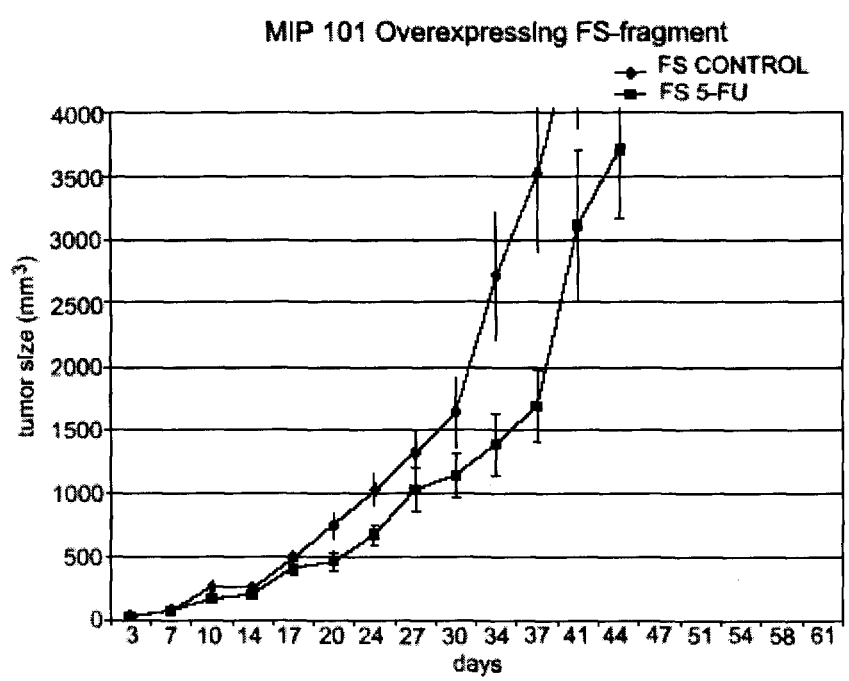
FIG. 9 shows the results of in vivo sensitization to the chemotherapeutic agent 5-FU as measured by tumor growth in a xenograft system comprising transplanted tumor cells expressing SEQ ID NO: 4/FS-Fragment (growth with and without 5-FU).
Figure 10:
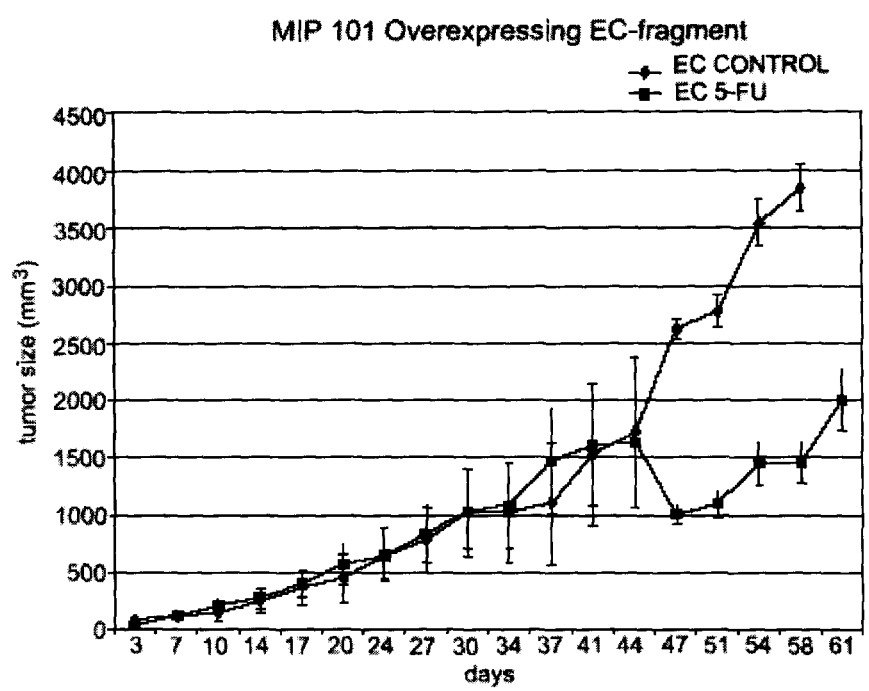
FIG. 10 shows the results of in vivo sensitization to the chemotherapeutic agent 5-FU as measured by tumor growth in a xenograft system comprising transplanted tumor cells expressing SEQ ID NO: 6/EC-Fragment (growth with and without 5-FU).

As a control, MIP101 cells sensitive and resistant to 5-FU (MIP/5FU) cells were exposed to peptides A (SEQ ID NO: 13); A1 (SEQ ID NO: 14); A2 (SEQ ID NO: 15); and A3 (SEQ ID NO: 16) as shown in FIG. 5, and to B8-SCR (SEQ ID NO: 17); and B14-SCR (SEQ ID NO: 18) as shown in FIG. 6. In both resistant and sensitive cells, the peptide (at high concentrations) alone or in combination with 5-FU, did not significantly affect % cell viability (FIGS. 5 and 6).

Example 3

Use of SPARC Peptide Chemosensitizers In Vivo

This example demonstrates A utility of the inventive SPARC peptide chemosensitizers in a tumor xenograft model system.

Tumor xenograft animal models were used to assess the effect of overexpressing different SPARC fragments on tumor progression in vivo. MIP 101 cells with stable transfection and expression of SPARC (MIP/SP) or different biological fragments representing the N-terminus (MIP/NT), follistatin (MIP/FS) and extracellular (MIP/EC) domains of SPARC were used for the tumor xenograft model. NIH nude mice (6 weeks old, Taconic Laboratories, Germantown, N.Y.) were implanted with $1 \times 10^6$ cells at the left flank. Treatment regimens were initiated once the average tumor size reached 75-100 $mm^3$ in volume. Tumors were measured using a handheld caliper (Fisher Scientific International, Inc. Hampton, N.H.) with concurrent body weight measurements until the completion of the study. Chemotherapy was provided using a 3-week cycle regimen (×6 cycles in total): 5-FU 25 mg/kg body weight intraperitoneal (IP) injections three times on week 1 of each cycle, followed by 2 weeks of treatment-free periods. Control animals received saline injections. Each group contained 6-8 animals.

The results are shown in FIGS. 7-10. MIP 101 cells stably expressing the N-terminus (NT-fragment; SEQ ID NO: 2) and extracellular (EC-fragment; SEQ ID NO: 6) domains of SPARC demonstrated significant sensitization to 5-FU in this xenotransplant system. Specifically, the NT-fragment appears to provide the greatest sensitivity in vivo, followed by the EC-fragment, and lastly, the FS-fragment. The EC-domain shows a delayed moderate chemosensitizing effect, which occurs after about 44 days of treatment in the present assay.

While specific embodiments of the invention have been described and illustrated, such embodiments should be considered illustrative of the invention only and not as limiting the invention.

The invention claimed is:

1. A method of sensitizing a cancerous cell to a cancer therapeutic agent, the method comprising:
   (a) delivering a polypeptide, consisting of an amino acid sequence selected from one or more of a peptide consisting of SEQ ID NO: 3, SEQ ID NO: 5, SEQ ID NO:7, SEQ ID NO: 8 and SEQ ID NO: 9; to a cell; and
   (b) treating the cell with the cancer therapeutic agent.

2. The method of claim 1, wherein the delivering and the treating are simultaneous.

3. The method of claim 1, wherein the delivering precedes the treating.

4. The method of claim 1, wherein the treating precedes the delivering.

5. The method of claim 1, wherein the cancer therapeutic agent is selected from the group consisting of one or more chemotherapeutic agents, one or more radiotherapeutic agents, one or more alternative therapeutic agents, and combinations thereof.

6. The method of claim 1, wherein the polypeptide consists of SEQ ID NO: 3.

7. The method of claim 1, wherein the polypeptide consists of SEQ ID NO: 5.

8. The method of claim 1, wherein the polypeptide consists of SEQ ID NO: 7.

9. The method of claim 1, wherein the polypeptide consists of SEQ ID NO: 8.

10. The method of claim 1, wherein the polypeptide consists of SEQ ID NO: 9.

11. The method of claim 1, wherein the cancerous cell is resistant to a therapeutic regimen.

* * * * *

UNITED STATES PATENT AND TRADEMARK OFFICE
CERTIFICATE OF CORRECTION

| | | |
|---|---|---|
| PATENT NO. | : 8,440,625 B2 | Page 1 of 1 |
| APPLICATION NO. | : 12/306804 | |
| DATED | : May 14, 2013 | |
| INVENTOR(S) | : Tai | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this
Thirtieth Day of December, 2014

Michelle K. Lee
*Deputy Director of the United States Patent and Trademark Office*